United States Patent [19]
Grinstaff et al.

[11] Patent Number: 5,508,021
[45] Date of Patent: Apr. 16, 1996

[54] NON-FLUORINATED POLYMERIC SHELLS FOR MEDICAL IMAGING

[75] Inventors: Mark W. Grinstaff, Pasadena; Neil P. Desai, Los Angeles, both of Calif.; Kenneth S. Suslick, Champaign, Ill.; Patrick Soon-Shiong; Paul A. Sandford, both of Los Angeles, Calif.; Noma R. Merideth, Pacific Palisades, Calif.

[73] Assignee: Vivorx Pharmaceuticals, Inc., Santa Monica, Calif.

[21] Appl. No.: 326,116

[22] Filed: Oct. 19, 1994

Related U.S. Application Data

[63] Continuation of Ser. No. 35,150, Mar. 26, 1993, Pat. No. 5,362,478.

[51] Int. Cl.$^6$ ............... A61B 5/055; A61B 8/13; A61K 49/04
[52] U.S. Cl. .......... 424/9.322; 424/9.42; 424/9.5; 436/173
[58] Field of Search ............ 424/9.37, 9.4, 424/9.42, 9.5, 9.322; 436/173; 128/653.4, 654

[56] References Cited

U.S. PATENT DOCUMENTS

| | | | |
|---|---|---|---|
| 4,639,364 | 1/1987 | Hoey | 424/9 |
| 4,832,941 | 3/1989 | Berwing et al. | 424/9.52 |
| 4,951,673 | 8/1990 | Long | 424/9 |
| 4,957,656 | 9/1990 | Cerny et al. | 424/9.52 |
| 5,114,703 | 5/1992 | Wolf et al. | 424/5 |
| 5,116,599 | 5/1992 | Roger, Jr. et al. | 424/9 |
| 5,143,716 | 9/1992 | Unger | 424/9 |
| 5,171,755 | 12/1992 | Kaufman et al. | 514/749 |
| 5,196,183 | 3/1993 | Yudelson et al. | 424/9.5 |
| 5,233,995 | 8/1993 | Yudelson et al. | 128/662.02 |
| 5,310,540 | 3/1994 | Giddey et al. | 424/9.52 |

FOREIGN PATENT DOCUMENTS

| | | |
|---|---|---|
| 0307863 | 3/1989 | European Pat. Off. |
| 0633030 | 1/1995 | European Pat. Off. |
| WO89/03693 | 5/1989 | WIPO |
| WO90/01953 | 3/1990 | WIPO |
| WO91/01759 | 2/1991 | WIPO |
| 91/15753 | 10/1991 | WIPO |
| 92/17213 | 10/1992 | WIPO |
| 92/18165 | 10/1992 | WIPO |

OTHER PUBLICATIONS

Edelman and Warach, "Magnetic Resonance Imaging (First of Two Parts)," *The New England Journal of Medicine* 328:708–716 (1993).

Edelman and Warach, "Magnetic Resonance Imaging (Second of Two Parts)," *The New England Journal of Medicine* 328:785–791 (1993).

Manning et al., "A Preliminary Report Comparing Magnetic Resonance Coronary Angiography with Conventional Angiography," *The New England Journal of Medicine* 328:828–832 (1993).

*Primary Examiner*—Gary E. Hollinden
*Attorney, Agent, or Firm*—Pretty, Schroeder, Brueggemann & Clark; Stephen E. Reiter

[57] ABSTRACT

In accordance with the present invention compositions comprising imaging agent(s) contained within polymeric shells are provided. Invention compositions are useful, for example, as contrast agents for magnetic resonance imaging (MRI), ultrasonography, and X-ray computer tomography. The polymeric shell diameter is typically approximately 2 microns in diameter. Consequently, these materials have organ specificity due to rapid scavenging by the reticuloendothial system (RES) or the mononuclear phagocyte (MNP) system upon intravenous injection. Furthermore, polymeric shells of the invention can be used to measure and monitor local oxygen and temperature. Exemplary contrast agents contemplated for use in the practice of the present invention include fluorinated compounds. Fluorinated compounds in general are hydrophobic and as such have limited water solubility. The invention method permits preparation of such compounds in a biocompatible form suitable for ready delivery.

23 Claims, No Drawings

NON-FLUORINATED POLYMERIC SHELLS FOR MEDICAL IMAGING

This is a continuing application of U.S. application Ser. No. 08/035,150, filed Mar. 26, 1993, U.S. Pat. No. 5,362, 478, the entire contents of which are hereby incorporated by reference herein.

FIELD OF THE INVENTION

The present invention relates to medical imaging, specifically to the use of contrast agents for magnetic resonance imaging (MRI), ultrasonography (US), and X-ray computer tomography (CT). In a particular aspect, contrast agent(s) is(are) entrapped in a polymeric shell formulated from a biocompatible polymer.

BACKGROUND OF THE INVENTION

In 1895, Roentgen (Nature 53:274–276 (1896)) discovered X-rays and their use to visualize bones and organs in a living body. In a typical experiment/diagnosis, X-rays would be directed to the patient and the resulting image would be collected on a film residing behind the patient. The developed film would show a qualitative picture of where the X-rays passed through the body. For example, soft tissues appear darker than dense structures such as bones, which absorb more of the X-rays. It was not until the 1970's, however, with the advent of computer technology coupled with X-ray technology, that this became a breakthrough in medical imaging (i.e., X-ray Computer Tomography; CT) (G. N. Hounsfield British Pat. 1283915; *Am. J. Radiol.* 131:103 (1978)). By using mathematical methods/models developed by A. M. Cormack (*J. Appl. Physics* 34:2722–2727 (1978)) one can reconstruct an image of the tissues that the X-rays have passed through. This ability to map tissue density (i.e., X-ray attention) allowed X-ray CT to become a common and routine medical diagnostic technique used world-wide today.

Contrast agents for X-rays have been used for a number of years. One of the first and by far one of the most extensively used X-ray contrast agents are barium salts. Barium salts are typically used for gastrointestinal imaging. Besides barium salts other radiopaque compounds are known. Essentially any organic molecule with one or more iodines or bromines will attenuate X-rays. This inherent property of the bromines and iodines allows compounds containing such atoms to be used as CT contrast agent. One particular class of CT contrast agents are brominated fluorocarbons such as perfluorooctylbromide (PFOB).

Perfluorooctylbromide has been effectively used in a number of indications as a CT contrast agent including: 1) determination of acute renal and hepatic microvascular volumes in acute renal failure (Hillman et al., *Invest Radiol.* 17:41–45 (1982)); 2) a liver/spleen specific tumor imaging agent (Mattrey et al., *Radiology* 145:755–758 (1982); Patronas et al., *Invest Radio.* 19:570– 573 (1984)); 3) PFOB blood pool contrast agent with imaging of the kidneys, liver, spleen, and mediastinum (Mattrey et al., *J. Comput. Assist. Tomogr.* 8:739–744 (1984); Peck et al., *Invest. Radiol.* 19:129–132 (1984)); 4) enhancement of liver abscesses with PFOB (Mattrey, R. F., *Invest. Radio.* 19:438–446, (1984); Mattrey et al., *Invest. Radiol.* 26:792– 798 (1991); Adam et Invest. Radial. 27:698–705 (1992)); 5) hepatosplenic computed tomography in humans with PFOB (Bruneton et al., *Invest. Radiol.* 23:306–307 (1988)); 6) determination of liver metastatic cancer in humans (Bruneton et al., *Radiology* 170:179–183 (1989)); 7) bronchiolography with PFOB (Stern et al., *J. Thorac. Imaging* 8:300–304 (1993)); and 8) GI imaging with PFOB (Mattrey et al., *Invest. Radiol.* 26:65–71 (1991)).

Indeed, contrast agents are desirable in radiological imaging because they enhance visualization of the organs (i.e., their location, size and conformation) and other cellular structures from the surrounding medium. The soft tissues, for example, have similar cell composition (i.e., they are primarily composed of water) even though they may have remarkably different biological functions (e.g., liver and pancreas).

The technique of magnetic resonance imaging (MRI) or nuclear magnetic resonance (NMR) imaging relies on the detection of certain atomic nuclei at an applied magnetic field strength using radio-frequency radiation. In some respects it is similar to X-ray computer tomography (CT), in that it can provide (in some cases) cross-sectional images of organs with potentially excellent soft tissue resolution. In its current use, the images constitute a distribution map of protons in organs and tissues. However, unlike X-ray computer tomography, MRI does not use ionizing radiation. MRI is, therefore, a safe non-invasive technique for medical imaging.

While the phenomenon of NMR was discovered in 1954, it is only recently that it has found use in medical diagnostics as a means of mapping internal structure. The technique was first developed by Lauterbur (*Nature* 242: 190–191 (1973)).

It is well known that nuclei with the appropriate nuclear spin align in the direction of the applied magnetic field. The nuclear spin may be aligned in either of two ways: with or against the external magnetic field. Alignment with the field is more stable; while energy must be absorbed to align in the less stable state (i.e. against the applied field). In the case of protons, these nuclei precess or resonate at a frequency of 42.6 MHz in the presence of a 1 tesla (1 tesla=104 gauss) magnetic field. At this frequency, a radio-frequency (RF) pulse of radiation will excite the nuclei and change their spin orientation to be aligned against the applied magnetic field. After the RF pulse, the excited nuclei "relax" or return to equilibrium or in alignment with the magnetic field. The decay of the relaxation signal can be described using two relaxation terms. $T_1$, the spin-lattice relaxation time or longitudinal relaxation time, is the time required by the nuclei to return to equilibrium along the direction of the externally applied magnetic field. The second, $T_2$, or spin-spin relaxation time, is associated with the dephasing of the initially coherent precession of individual proton spins. The relaxation times for various fluids, organs and tissues in different species of mammals is well documented.

One advantage of MRI is that different scanning planes and slice thicknesses can be selected without loss of resolution. This permits high quality transverse, coronal and sagittal images to be obtained directly. The absence of any mechanical moving parts in the MRI equipment promotes a high degree of reliability. It is generally believed that MRI has greater potential than X-ray computer tomography (CT) for the selective examination of tissues. In CT, the X-ray attenuation coefficients alone determine the image contrast, whereas at least three separate variables ($T_1$, $T_2$, and nuclear spin density) contribute to the magnetic resonance image.

Due to subtle physio-chemical differences among organs and tissue, MRI may be capable of differentiating tissue types and in detecting diseases that may not be detected by X-ray or CT. In comparison, CT and X-ray are only sensitive to differences in electron densities in tissues and organs. The images obtainable by MRI techniques can also enable a physician to detect structures smaller than those detectable by CT, due to its better spatial resolution. Additionally, any imaging scan plane can be readily obtained using MRI techniques, including transverse, coronal and sagittal.

Currently, MRI is widely used to aid in the diagnosis of many medical disorders. Examples include joint injuries, bone marrow disorders, soft tissue tumors, mediastinal invasion, lymphadenopathy, cavernous hemangioma, hemochromatosis, cirrhosis, renal cell carcinoma, uterine leiomyoma, adenomyosis, endometriosis, breast carcinomas, stenosis, coronary artery disease, aortic dissection, lipomatous hypertrophy, atrial septum, constrictive pericarditis, and the like (see, for example, Edelman & Warach, *Medical Progress* 328:708–716 (1993); Edelman & Warach, *New England J. of Medicine* 328:785–791 (1993)).

Routinely employed magnetic resonance images are presently based on proton signals arising from the water molecules within cells. Consequently, it is often difficult to decipher the images and distinguish individual organs and cellular structures. There are two potential means to better differentiate proton signals. The first involves using a contrast agent that alters the $T_1$ or $T_2$ of the water molecules in one region compared to another. For example, gadolinium diethylenetriaminepentaacetic acid (Gd-DTPA) shortens the proton $T_1$ relaxation time of water molecules in near proximity thereto, thereby enhancing the obtained images.

Paramagnetic cations such as, for example, Gd, Mn, and Fe are excellent MRI contrast agents, as suggested above. Their ability to shorten the proton $T_1$ relaxation time of the surrounding water enables enhanced MRI images to be obtained which otherwise would be unreadable.

The second route to differentiate the individual organs and cellular structures is to introduce another nucleus for imaging (i.e., an imaging agent). Using this second approach, imaging can only occur where the contrast agent has been delivered. An advantage of this method is the fact that imaging is achieved free from interference from the surrounding water. Suitable contrast agents must be bio-compatible (i.e. non-toxic, chemically stable, not reactive with tissues) and of limited lifetime before elimination from the body.

Although hydrogen has typically been selected as the basis for MRI scanning (because of its abundance in the body), this can result in poorly imaged areas due to lack of contrast. Thus the use of other active MRI nuclei (such as fluorine) can, therefore, be advantageous. The use of certain perfluorocarbons in various diagnostic imaging technologies such as ultrasound, magnetic resonance, radiography and computer tomography has been described in an article by Mattery (see SPIE, 626, XIV/PACS IV, 18–23 (1986)). The use of fluorine is advantageous since fluorine is not naturally found within the body.

Prior art suggestions of fluorine-containing compounds useful for magnetic resonance imaging for medical diagnostic purposes are limited to a select group of fluorine-containing molecules that are water soluble or can form emulsions. Accordingly, prior art use of fluorocarbon emulsions of aqueous soluble fluorocarbons suffers from numerous drawbacks, for example, 1) the use of unstable emulsions, 2) the lack of organ specificity and targeting, 3) the potential for inducing allergic reactions due to the use of emulsifiers and surfactants (e.g., egg phophatides and egg yolk lecithin), 4) limited delivery capabilities, and 5) water soluble fluorocarbons are quickly diluted in blood after intravenous injection.

Another medical imaging application for perfluorocarbon filled polymeric shells is ultrasonography. This non-invasive, non-iodizing radiation medical imaging technique is safe and currently used world-wide for a number of indications. Ultrasonic imaging (i.e., sonography) is based on the reflection of ultrasonic sound waves from an object. Thus, the acoustic properties of the material will have dramatic effects on the reflected (i.e., scattered) radiation or sound waves. The reflected or scattered ultrasound radiation is received by a probe that covers the area to be imaged. In a typical medical diagnosis, an ultrasonic transducer (ultrasonic frequency is typically in the MHz region) transmits ultrasound into a living body for which one wishes to obtain an image or diagnosis. The ultrasound travels through the region and scatters on structures (e.g., organs). This scattered ultrasound is then collected and an image is produced.

The magnitude of the reflected sound waves is dramatically dependent on the acoustic properties of the material. The acoustic properties of a substance depend both on the density as well as the velocity of the transmitted ultrasound. Materials typically have their greatest differences of acoustic properties at interfaces such as liquid-gas or liquid-solid. This difference in acoustic properties (i.e., the acoustic impedance) results in more intense reflected ultrasonic radiation. In a physical sense the reflected sound waves are influenced by the following: 1) the size of the scattering center, 2) the differences in density from the scattering center and the surrounding area, 3) the compressibility of the scattering center, and 4) the acoustic properties of the surrounding area. However, the scattered ultrasound that is received from an image and processed often lacks signal intensity, sharpness and clarity. Thus, contrast agents that will help to distinguish organs and tissues are of great need. By using materials that have different acoustic properties than the surrounding area it is possible to improve the resolution of the acquired image. One class of materials that have been used as ultrasonography contrast agents are perfluorohalocarbons.

Another medical imaging application for polymeric shells is electron paramagnetic resonance (EPR) imaging and spectroscopy. This non-invasive, non-iodizing radiation medical spectroscopy and imaging technique is safe and currently in preclinical development.

In order for EPR spectroscopy and imaging to be accomplished, the nitroxide free radical needs to be detected by the EPR instrument. However most nitroxide free radicals are not stable in vivo because they are bioreduced. This short half-life in vivo prevents this technique from being used for imaging. Yet, this technique has better sensitivity than magnetic resonance imaging and thus would be a medically useful technique. Accordingly, means to protect nitroxide free radicals from bioreduction by the in vivo environment would be of great value.

BRIEF DESCRIPTION OF THE INVENTION

In accordance with the present invention, there are provided compositions useful for obtaining magnetic resonance images of organs and tissues of the body. Invention compositions comprise imaging agents entrapped in a biocompatible polymer shell. Also provided are methods for entrapping imaging agents in a polymeric shell. Still further in accordance with the present invention, there are provided means for obtaining local oxygen and temperature data, and for obtaining fluorine and/or proton magnetic resonance images, ultrasonography and X-ray computer tomography of body organs and tissues.

For example, a suspension of polymeric shells of the invention can be administered intravenously, making imaging of the vascularized organs (e.g., liver, spleen, and lung) and bone marrow possible. Organ target specificity is achieved as a result of uptake of the micron-sized polymeric shells (containing imaging agent) by the reticuloendothelial system (RES) (also known as the mononuclear phagocyte (MNP) system). Organs such as the liver and spleen play an important role in removing foreign species (e.g., particulate matter) from the bloodstream, and hence are often referred to as the "blood filtering organs". These organs make up a major part of the RES. In addition, lymph nodes within the lymphatic circulation contain cells of the RES. Consequently, imaging of the lymphatic system is possible employing micron-sized polymeric shells of the present invention (containing imaging agent). Given orally or as a suppository, imaging of the stomach and gastrointestinal tract can be carried out. Such suspensions can also be injected into non-vascular space, such as the cerebro-spinal cavity, allowing imaging of such space as well.

As a further embodiment of the present invention, paramagnetic cations such as Gd, Mn, Fe, and the like can be bound to polyanions, such as alginate, and used as an effective MRI contrast agent.

The present invention overcomes the drawbacks of the prior art by providing 1) injectable suspensions of polymeric shells containing imaging agents, 2) imaging agents in a form having enhanced stability compared to simple emulsions, 3) organ targeting specificity (e.g., liver, spleen, lung etc.) due to uptake of the polymeric shells of the invention by the RES or MNP system, 4) emulsifier-free system, thereby avoiding agents that may potentially cause allergic reactions, and 5) the ability to inject relatively small doses and still acquire good images because the polymeric shells of the invention (containing imaging agents) are concentrated in the targeted organ.

DETAILED DESCRIPTION OF THE INVENTION

In accordance with the present invention, there are provided compositions for obtaining in vivo medical diagnostic images, said composition comprising an imaging agent(s) substantially completely contained within a polymeric shell.

As used herein, the term "imaging agent" refers to any compound or combination of compounds which enhance the visualization (and, therefore, the differentiation) of organs and other cellular structures from the surrounding medium. As used herein, the term imaging agent embraces contrast agents, such as organofluorine compounds, oils, paramagnetic compounds, paramagnetic or superparamagnetic particles, stable free radicals, and the like.

In accordance with one aspect of the present invention, it has been found that organofluorine-containing compounds, which in general are hydrophobic, water immiscible and consequently difficult to administer, can be entrapped in polymeric shells for ease of delivery. Organofluorine-containing compounds entrapped within polymeric shells are readily usable and biocompatible. The particle size of polymeric shells produced in accordance with the present invention have an average diameter of approximately 2 microns, which is ideal for medical applications, since intravenous or intraarterial injections can be accomplished without risk of small blood vessel blockage and subsequent tissue damage (e.g., caused by ischemia due to oxygen deprevation). For comparison, red blood cells are approximately 8 microns in diameter (thus injectable biomaterial should be smaller than 8–10 microns in diameter to prevent blood vessel blockage).

The high concentration of fluorine (and the consequent lack of protons) in the polymeric shell facilitates the use of this material as an effective fluorine ($^{19}F$) magnetic resonance imaging contrast agent. Alternatively, this lack of protons also allows this contrast agent to be a suitable proton contrast agent. Performing a typical proton magnetic resonance scan highlights the region where there is a lack of protons (generated by the presence of fluorine) and allows imaging of the desired area. Consequently, it is possible to image where this polymeric shell contrast agent resides within the body as a diamagnetic T2 agent. Thus, this unique polymeric shell containing any number of different fluorocarbons can be used as both a $^{19}F$ and a $^{1}H$ magnetic resonance contrast agent.

Naturally occurring fluorine atoms ($^{19}F$) give a clear nuclear magnetic resonance signal and thus can function as contrast agents or "probes" in MRI. The specific advantages for the use of $^{19}F$ include: 1) an extremely low native concentration in the body (fluorine is not naturally found in the body), 2) a high nuclear magnetic resonance sensitivity, 3) a magnetogyric ratio close to that of $^{1}H$, thus permitting $^{19}F$ magnetic resonance imaging to be carried out with only minor modifications of existing MRI devices, and 4) low toxicity of the organofluorine-containing compounds.

In general, fluorocarbons are non-toxic and biocompatible. Fluorocarbons are stable and unreactive, and consequently are not likely to be metabolized due to their strong carbon-fluorine bonds (approximately 130 kcal/mole). For comparison, carbon-hydrogen bonds (approximately 100 kcal/mole) are weaker and much more reactive. The FDA has approved two fluorocarbons, perfluorotripropyl amine and perfluorodecalin, for medicinal use as blood substitutes under the trade name of Fluosol DA.

A number of different fluorocarbons can be used in the practice of the present invention. For example, compounds satisfying the following generic formulae can be incorporated into polymeric shells employing the invention procedure as described herein:

(a) $C_xF_{2x+y-z}A_z$, wherein:

x=1–30, preferably 5–15, y=2; or 0 or –2, when $x \geq 2$; or –4 when $x \geq 4$, z=any whole number from 0 up to (2x+y–1), and A is selected from H, halogens other than F, —CN, —OR,
  wherein R is H, alkyl, fluoroalkyl, alkenyl, fluoroalkenyl, alkynyl, fluoroalkynyl, aryl, fluoroaryl, alkanoyl, fluoroalkanoyl, alkenoyl, fluoroalkenoyl, alkynoyl, fluoroalkynoyl, (b) $[C_xF_{2x+y'-z}A_z]_aJR_{b-a}$, wherein:

x, z, A and R are as defined above, y'=+1; or –1 or –3, when $x \geq 2$; or –5 when $x \geq 4$, J=O, S, N, P, Al, or Si, a=1, 2, 3, or 4, and b=2 for a divalent J, or
  3 for a trivalent J,
  4 for a tetravalent J, (c) $A'–[(CF_2)_x–O]_c–A''$, wherein:

x is as defined above,

A' is selected from H, halogens, —CN, —OR,
  wherein R is H, alkyl, fluoroalkyl, alkenyl, fluoroalkenyl, alkynyl, fluoroalkynyl, aryl, fluoroaryl, alkanoyl, fluoroalkanoyl, alkenoyl, fluoroalkenoyl, alkynoyl, fluoroalkynoyl, A" is selected from H or R, wherein R is as defined above, c=1–200, preferably 2–50, or (d) 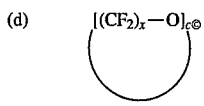

wherein:
x is as defined above, and
c'=2–20, preferably 2–8,
as well as mixtures of any two or more thereof.

Included within the above generic formulae are compounds having general formulae such as:

$C_xF_{2x}$, such as, for example, perfluoro-1-hexene ($C_6F_{12}$), perfluoro-2-hexene ($C_6F_{12}$), perfluoro-3-hexene ($C_6F_{12}$), and the like, cyclo-$C_xF_{2x}$, such as, for example, perfluorocyclohexane ($C_6F_{12}$), perfluorocyclooctane ($C_8F_{16}$), and the like, $C_xF_{2x-2}$, such as, for example, perfluoro-1-hexyne ($C_6F_{10}$), perfluoro-2-hexyne ($C_6F_{10}$), perfluoro-3-hexyne ($C_6F_{10}$), and the like, bicyclo-$C_xF_{2x-2}$, such as, for example, perfluorodecalin ($C_{10}F_{18}$), and the like, $C_xF_{2x+2}$, such as, for example, perfluorononane ($C_9F_{20}$), perfluorodecane ($C_{10}F_{22}$), perfluorododecane ($C_{12}F_{26}$), and the like, $C_xF_{2x-4}$, such as, for example, perfluoro-2,4-hexadiene, and the like, $C_xF_{2x+1}A$, such as, for example, perfluorotripropyl amine $[(C_3F_7)_3N]$, perfluorotributyl amine $[(C_4F_9)_3N]$, perfluoro-tert-tributyl amine, and the like, $C_xF_{2x-2}A_2$, such as, for example, $C_{10}F_{18}H_2$, and the like.

Besides linear, branched-chain and cyclic fluorine-containing compounds as noted above, fluorinated crown ethers (such as, for example, perfluoro 12-crown-4, perfluoro 15-crown-5, perfluoro 18-crown-6, and the like) are also contemplated for use in the practice of the present invention.

In order to obtain good magnetic resonance images with high signal to noise ratios, it is advantageous to have a high number of equivalent fluorines. As used herein, the term "equivalent fluorines" refers to those fluorine substituents of a fluorine-containing compound which exist in a substantially similar micro-environment (i.e., substantially similar magnetic environment). Equivalent fluorines will produce one imaging signal. A high number of equivalent fluorines will produce a strong signal, undiluted by competing signals of "non-equivalent" fluorines.

As used herein, the term "non-equivalent fluorines" refers to those fluorine substituents of a fluorine-containing compound which exist in a substantially dis-similar micro-environment (i.e., substantially dissimilar magnetic environment), relative to other fluorine substituents on the same fluorine-containing compound. Thus, in contrast to equivalent fluorines, non-equivalent fluorines will give multiple signals due to their different chemical shifts. Thus, while compounds with a large number of non-equivalent fluorines are satisfactory for MRI applications, such compounds are not ideal for maximum imaging.

To overcome the problems with using fluorinated compounds that do not have equivalent fluorines, image acquisition routines have been developed which correct for chemical shift artifacts. However, since not all of the fluorines are used to acquire the image, the fluorinated material is not ideal for optimum image acquisition. Several different acquisition routines have been developed for collecting $^{19}F$ magnetic resonance images with PFOB to correct for the chemical-shift artifacts that arise from the magnetically non-equivalent fluorine on PFOB (see, for example, Lee, H. K., *Magn. Reson. Med.* 23:254–263 (1992); Ozdemirel, B., *Magn. Reson. Med.* 23:324–332 (1992); Lee et al., *J. Magn. Reson. Imaging* 2:53–61 (1992); and Noth et al., *Magn. Reson. Imaging* 12:149–153 (1994)).

The fluorocarbon contained within the polymeric shell represents a substantially different environment than the protons in the surrounding tissues, cells and blood. This difference is also noted in the T1 and T2 relaxation properties of the two materials: fluorocarbons and water. Encapsulation of other materials, besides fluorocarbons, which have different proton relaxation properties will also be suitable T2 contrast agents. For example encapsulation of soybean oil (USP) in the polymeric shell will also produce a T2 weighted contrast agent. The encapsulated material is not limited to soybean oil. A number of other materials are suitable including mineral oil, corn oil, rapeseed oil, coconut oil, olive oil, safflower oil, cotton seed oil, and the like. Non-natural materials are also contemplated, including fluorinated organic compounds (as discussed above), Olestra (a non absorbing fat; produced by Proctor & Gamble), polyalkylene glycols, and the like. Olestra by itself has been shown to be an adequate T2 contrast agent (Magin et al., *Mag. Res. Med.* 19: 199 (1991)).

Besides diamagnetic T2 contrast agents, the polymeric shells of the invention can be used as ferromagnetic or paramagnetic magnetic resonance contrast agents. These agents introduce a local magnetic field where they are present and consequently change the relaxation properties of the protons that are nearby. This change in proton T1 and T2 allows for these contrast agents to be used in the typical proton analysis. Most often a T1 weighted proton imaging sequence is used. Encapsulation of small ferromagnetic or superparamagnetic metal particles (e.g., Fe, Mn, and the like) into the polymeric shells enable this to be used as a contrast agent. For example, small (3 to 10 nm) particles of iron oxide can be dispersed in a fluorocarbon (or soybean oil, or other suitable medium) and then entrapped within a polymeric shell according to the present invention.

Altering the local magnetic field by introducing small iron particles is one means to provide proton differentiation. This differentiation allows for contrast proton imaging to occur. An alternative to iron particles is to use a polymeric shell composed of an iron containing protein, such as hemoglobin. This hemoglobin polymeric shell may contain either a liquid (perfluorocarbon, soybean oil, and the like) or may be gas (argon, nitrogen, helium, and the like). This iron containing protein in vivo functions to deliver oxygen to the cell. This protein has paramagnetic properties in both its $Fe^{+2}$ deoxy state and $Fe^{+3}$ state. This paramagnetic property will introduce a local magnetic field and disrupt the original magnetic field present. Single molecules of deoxy hemoglobin (as opposed to hemoglobin-polymeric shells according to the present invention that contain approximately $10^7$ Hb molecules crosslinked together) have been previously used as a paramagnetic susceptibility contrast agent (Ogawa et al., *Mag. Reson. Med.* 14:68 (1990); Turner et al., *Magn. Reson. Med.* 22:159 (1991); Wendland et al., *SMR Meeting Abstract # 391* (1994), San Francisco, Calif.). However, these studies were limited by the lack of a high concentration of deoxyhemoglobin and thus monomeric hemoglobin molecules are not optimal as a contrast agent. Consequently, polymeric shells of the invention that contain many hemoglobin molecules should exert a larger magnetic field and provide for improved proton imaging.

Another variation of the polymeric shells as magnetic resonance imaging contrast agents is to use an aqueous filled gluten polymeric shell that contains a water soluble contrast agent such as GD-DTPA, Dy-DTPA, Gd-DOPA, and the like. These complexes, as well as similar ones, can be dissolved in saline followed by encapsulation into the gluten polymeric shell. The pore size of the gluten microsphere is such that large molecular weight compounds (>100 MW) such as the Gd-complexes will not leak out, and consequently the water molecules that reside in the polymeric shell with the Gd-complex are distinguishable under magnetic resonance imaging conditions. Thus the entire polymeric shell is a suitable proton magnetic resonance imaging contrast agent.

The use of invention compositions for oxygen detection is based upon the dramatic changes in NMR relaxation rate of $^{19}F$ in the presence of a paramagnetic species such as oxygen. Since oxygen is paramagnetic, it will interact with the fluorine nucleus, increasing the relaxation rate of $^{19}F$ from the excited state to the normal state. By monitoring this change in relaxation rate, it is possible to determine the oxygen concentration in a local area (by calibrating the MRI signal to a known concentration of oxygen).

The novelty of this system lies, for example, in 1) the use of MRI to obtain oxygen information, 2) the use of the oxygen paramagnetic influence on the $^{19}F$ MRI (NMR) signal, 3) the use of polymeric shells to provide a constant and protective environment that is also permeable to oxygen, and the like.

By using imaging agents that are capable of undergoing a phase transition over physiological temperature ranges (e.g., high molecular weight compounds, or combinations of fluorine-containing compounds), MRI can also be used to measure local temperature. Thus, imaging agents which undergo a solid to liquid phase transition, a liquid to gas phase transition or a liquid to solid phase transition can be employed. Relaxation times are much longer in solids than in liquids (or in liquids relative to gases). Thus relaxation times will decrease dramatically as the transition temperature (i.e., from solid to liquid, or liquid to gas) is reached. Dramatic changes are observed in the NMR spectrum during phase transition of solid to liquid (as well as the phase transition from liquid to gas, or liquid to solid). The shape of the MRI signal for a given imaging agent can be calibrated to a known temperature. For example, by using a high molecular weight imaging agent within the polymeric shell (e.g., a fluorine-containing compound having a melting point of $\geq 15°$ C.), or by using a combination of imaging agents within the polymeric shell (e.g., a combination of a fluorine-containing compound with a non-fluorinated compound within the polymeric shell), the contents of the interior of the polymeric shell can be selected so as to provide a desired temperature range for phase transition to occur (typically in the range of about 22°–55° C.). The imaging agents within the shell will undergo a phase transition over the desired temperature range, altering substantially the observed relaxation rates, thus permitting in vivo temperature determination. Local temperature information would be especially useful, for example, in monitoring cancer patients during the hyperthermia treatment of cancer or in the detection of cancer cells (cancer cells are cooler than normal cells).

The composition employed will determine the temperature range of the phase transition. Thus, this technique can be used over a wide temperature range, simply by changing the makeup of the imaging agent composition. For example, pure perfluoro-dodecane ($C_{12}F_{26}$) entrapped in a polymeric shell will undergo a solid to liquid phase transition at the melting point of the fluorocarbon (75° C.) However, this transition would be sharp and only a small amount of temperature information would be obtained. To obtain greater information, the melting point of the imaging agent composition can be spread over a wider range, for example, by simply adding another component to the pure imaging agent composition. It is well known in the art that a mixture will have a lower and broader melting point range than the corresponding pure components. Accordingly, for example, formulating (i.e., mixing) perfluorododecane with a lower molecular weight fluorocarbon will broaden the melting point range of the encapsulated composition.

In addition, chemically modified long chain fatty acids (e.g., heptadecanoic acid $[C_{17}H_{34}O_2]$, nonadecanoic acid $[C_{19}H_{38}O_2]$, and the like), alcohols (e.g., nonadecanol $[C_{19}H_{40}O]$, docosanol $[C_{22}H_{46}O]$, and the like) to which fluorines can chemically be added can also be used in the practice of the present invention. For example, a dehydration coupling reaction between perfluoro-tertbutanol ($t$-$C_4F_9$-OH; PCR CHEMICALS) with any of the above-described reactive oxygen-containing compounds will produce a molecule that undergoes a solid to liquid phase transition and one that has nine equivalent fluorines. Similarly, a mixture of a fluorinated fatty acid and cholesterol, for example, will broaden the melting point range compared to the pure fluorinated fatty acid, thereby allowing for local temperature measurements to be made.

The novelty of this temperature detection system lies, for example, 1) in the use of MRI to obtain spatially resolved temperature information, 2) in the use of the temperature dependence of the MRI (NMR) signal, 3) in the use of a fluorocarbon-containing composition that undergoes a solid to liquid phase transition in the desired temperature range, 4) in the use of the polymeric shell to provide a constant and protective environment for the medium, and 5) in the ability to obtain temperature information simultaneously with morphology information.

Ultrasonography contrast agents can be developed with polymeric shells of the invention (i.e., filled with fluorocarbon contrast agent). For example, perfluorohalocarbons such as perfluorooctylbromide (PFOB) have properties that are significantly different than water, tissues, organs, and bones. One such property is density. PFOB has a density of approximately 1.8 g/mL and is significantly different than water (one of the main components of tissues and organs; density approximately 1.0 g/mL) and simple organic materials (such as oils, hexane; density <1.0 g/mL). Density is one property of materials that will effect acoustic scattering. The acoustic properties and the ability of PFOB to be a contrast agent for ultrasonic imaging are outlined by Andre et al., (*Invest. Radiol.* 25:983–987 (1990)). Thus, polymeric shells of the present invention filled with fluorocarbons can be used as contrast agents for X-ray computer tomography, magnetic resonance imaging and ultrasonography.

Perfluorooctylbromide has been used effectively as an ultrasound agent in a number of indications including: 1) imaging specific tumors in the liver and spleen with PFOB (Mattrey et al., *Radiology* 145:759–762 (1982)); 2) imaging the liver with perfluorodecalin and perfluorotripropylamine (Mattrey, R. F. J., *Ultrasound Med.* 2:173–176 (1983)); 3) evaluating acute myocardial infarction with PFA and PFOB (Mattrey, R. F. and Andre, M. P., *Am. J. Cardiol.* 54:206–210 (1984); and 4) detecting kidney function and acute tubular necrosis (Munzing et al., *Kidney Int.* 39:733–739 (1991); Coley, B. D., *Kidney Int.* 39:740–745 (1991)).

Besides PFOB encapsulated in a polymeric shell, smaller molecular weight fluorocarbons are equally valuable. For example, perfluoropentane can be encapsulated into the polymeric shell. This perfluorocarbon is a liquid at room temperature, however at 37° C. it is a gas. Thus, when injected, the perfluorocarbon in the polymeric shell will undergo a phase transition, i.e., from liquid to gas. This change in physical state will attenuate the ultrasonic waves, producing good contrast. Thus, perfluoropentane and the like encapsulated in polymeric shells will be good contrast agents.

Perfluorohalocarbons, such as perfluorooctylbromide (PFOB), are also radiopaque and can be used as contrast agents for X-ray computer tomography. Thus, polymeric shells filled with brominated or iodinated fluorocarbons can be used as contrast agents for X-ray computer tomography as well as magnetic resonance imaging. The advantage of being both an MRI as well as an x-ray contrast agent renders polymeric shells of the invention cost effective for hospitals, and thus enhances the likelihood that such agents will be more widely used by physicians.

Another medical imaging application for polymeric shells is in electron paramagnetic resonance (EPR) imaging and spectroscopy. This non-invasive, non-iodizing radiation medical spectroscopy and imaging technique is safe and currently in preclinical development. Encapsulating nitroxides in polymeric shells of the present invention provides a number of advantages. First, the polymeric shell protects the nitroxide, and thus the encapsulated nitroxide is no longer subject to bioreduction in vivo. Suspensions containing nitroxide free radicals in a polymeric shell can then be injected in vivo (less than a 10% loss in signal is observed over an hour).

Nitroxides also have properties that make them ideally suited for medical imaging. First, their signal is sensitive to oxygen. Thus the signal (i.e., the signal line-width) can be calibrated to a known oxygen concentration. It would then be possible to generate oxygen distribution maps of tissues and organs using this technique. For example, this would be helpful/useful in the detection and diagnosis of tumors.

secondly, the nitroxide free radical signal is sensitive to its surrounding physical state. For example, in a solid the observed EPR signal is very broad. This same nitroxide, when dissolved in a liquid, shows a typical sharp spectrum. By dissolving the nitroxide in a mixture that melts in a suitable temperature range, one can generate a temperature-EPR signal calibration curve. The nitroxide will dissolve in mixtures, but not in pure materials. This allows for a wide temperature range to be observed and furthermore the temperature transition is not sharp. An example of a mixture to be used for dissolving nitroxide is a cholesterol/fatty acid mixture. By selecting the correct fatty acid, one can design systems that melt over a wide range of temperatures (10°–70° C.).

Fluorine-containing compounds entrapped in polymeric shells according to the present invention can be used for a variety of purposes, e.g., to obtain magnetic resonance images of various organs and/or tissues, to obtain oxygen profiles in organs and/or tissues, and also to measure local temperature. Invention contrast agents are not limited to use in MRI applications, but can also be used for such applications as ultrasonography and radiology. The other isotope of fluorine, $^{18}F$, can be used as a positron emission tomography (PET) contrast agent. Thus, with one fluorine-containing contrast agent, both PET and MRI diagnosis can be accomplished. Entrapment of other imaging agents, such as technetium and thallium compounds that are used in radiocontrast media, is also possible. Two examples of such contrast agents include Neurolyte and cardiolyte.

A number of biocompatible polymers may be employed in the practice of the present invention for the formation of the polymeric shell which surrounds the fluorine-containing composition. As used herein, the term "biocompatible" describes a substance that does not appreciably alter or affect in any adverse way, the biological system into which it is introduced. Essentially any polymer, natural or synthetic, bearing sulfhydryl groups or disulfide bonds within its structure may be utilized for the preparation of a disulfide crosslinked shell around the fluorine-containing composition. The sulfhydryl groups or disulfide linkages may be preexisting within the polymer structure or they may be introduced by suitable chemical modification. For example, natural polymers such as proteins, lipids, oligopeptides, polypeptides, polynucleic acids, polysaccharides (e.g., starch, cellulose, dextrans, alginates, chitosan, pectin, hyaluronic acid, and the like), and so on, are candidates for such modification.

As examples of suitable biocompatible polymers, naturally occurring or synthetic proteins may be employed, so long as such proteins have sufficient cysteine residues within their amino acid sequences so that crosslinking (through disulfide bond formation, for example, as a result of oxidation during ultrasonic irradiation) can occur. Examples of suitable proteins include albumin (which contains 35 cysteine residues), insulin (which contains 6 cysteines), hemoglobin (which contains 6 cysteine residues per $\alpha_2\beta_2$ unit), lysozyme (which contains 8 cysteine residues), immunoglobulins, $\alpha$-2-macroglobulin, fibronectin, vitronectin, fibrinogen, gluten, lipase, and the like.

A presently preferred protein for use in the formation of a polymeric shell is albumin. Optionally, proteins such as $\alpha$-2-macroglobulin, a known opsonin, could be used to enhance uptake of the shell encased particles of substantially water insoluble pharmacologically active agents by macrophage-like cells, or to enhance the uptake of the shell encased particles into the liver and spleen.

Similarly, synthetic polypeptides containing cysteine residues are also good candidates for formation of a shell around the substantially water insoluble pharmacologically active agents. In addition, polyvinyl alcohol, polyhydroxyethyl methacrylate, polyacrylic acid, polyethyloxazoline, polyacrylamide, polyvinyl pyrrolidinone, and the like, are good candidates for chemical modification (to introduce sulfhydryl and/or disulfide linkages) and shell formation (by causing the crosslinking thereof).

In the preparation of invention compositions, one can optionally employ a dispersing agent to suspend or dissolve the imaging agent. Dispersing agents contemplated for use in the practice of the present invention include any non-aqueous liquid that is capable of suspending or dissolving the imaging agent, but does not chemically react with either the polymer employed to produce the shell, or the imaging agent itself. Examples include vegetable oils (e.g., soybean oil, mineral oil, corn oil, rapeseed oil, coconut oil, olive oil, safflower oil, cotton seed oil, and the like), aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 2–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CH_2Cl$—$CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Imaging agents contained within a polymeric shell, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

In accordance with another embodiment of the present invention, there is provided a method for the preparation of imaging agents for in vivo delivery, said method comprising subjecting aqueous medium containing biocompatible polymer capable of being crosslinked by disulfide bonds and imaging agent to high intensity ultrasound (and/or free radical generating) conditions for a time sufficient to promote crosslinking of said biocompatible polymer by disulfide bonds;

wherein said agent is substantially completely contained within a polymeric shell, wherein the largest cross-sectional dimension of said shell is no greater than about 10 microns, and wherein said polymeric shell containing agent therein is suspended in a biocompatible aqueous liquid for in vivo delivery.

Thus, in accordance with the present invention, imaging agents contained within polymeric shells can be synthesized using emulsification and/or cavitation and/or free radical generation. An example of a process that provides both emulsification and cavitation is high intensity ultrasound. Ultrasound generates two non-linear acoustic processes (i.e., acoustic emulsification and cavitation). Ultrasound, which spans the frequencies from a few kilohertz to megahertz, can be used to produce polymeric shells containing imaging agents. A frequency of 20 Khz enables many suspensions to be formed as illustrated in the examples which follow. First, acoustic emulsification disperses the imaging agents into the aqueous protein solution. The dispersion formed is then concurrently or post chemically crosslinked by highly reactive species (e.g., superoxide) that are produced by cavitation when oxygen is present. Cavitation is the formation, growth and collapse of bubbles in a solution. Cavitation is well known to be generated during many processes besides ultrasound (e.g., turbulent flow and mixing). The reactive species then cross-links and stabilizes the dispersion/suspension through the formation of disulfide bonds. The disulfide bonds are formed from the cysteine residues (in the case that the polymer is a protein such as albumin) that are in the protein being treated.

Alternatively, those skilled in the art recognize that the above-described process can be separated into multiple steps, and need not be carried out as a single ultrasonic procedure. First the imaging agents can be dispersed, followed by protein (disulfide) cross-linking to form the stable polymeric shell. Suitable dispersion techniques include stirring, homogenizing, microfluidizing, ultrasonic irradiation, and the like. The intra and inter protein crosslinking via reactive species such as $O_2$ can be generated by chemical reaction ($KO_2$), electrochemical reaction, photochemical reaction, thermal reaction, biochemical reaction (e.g., flavor proteins, xanthine oxidase), ultrasonic reaction, turbulent flow, and the like.

As used herein, the term "in vivo delivery" refers to delivery of imaging agents by such routes of administration as oral, intravenous, subcutaneous, intraperitoneal, intrathecal, intramuscular, inhalational, topical, transdermal, nasal, suppository (rectal), pessary (vaginal), and the like.

A non-obvious feature of the above-described process is in the choice of dispersing agent, specifically with respect to the polarity of the dispersing agent. The formation of a shell around particles of imaging agent involves the unfolding and reorientation of the polymer at the interface between the aqueous and non-aqueous phases such that the hydrophilic regions within the polymer are exposed to the aqueous phase while the hydrophobic regions within the polymer are oriented towards the non-aqueous phase. In order to affect the unfolding of the polymer, or change the conformation thereof, energy must be supplied to the polymer. The interfacial free energy (interfacial tension) between the two liquid phases (i.e., aqueous and non-aqueous) contributes to changes in the polymer conformation at that interface. Thermal energy also contributes to the energy pool required for the unfolding and/or the change of polymer conformation.

Thermal energy input is a function of such variables as the acoustic power employed in the high intensity ultrasound process, the exposure time to high intensity ultrasound, the nature of the material being subjected to high intensity ultrasound, the volume of the material being subjected to high intensity ultrasound, and the like. The acoustic power of high intensity ultrasound processes can vary widely, typically falling in the range of about 1 up to 1000 watts/$cm^2$; with an acoustic power in the range of about 50 up to 200 watts/$cm^2$ being a presently preferred range. Similarly, exposure time to high intensity ultrasound can vary widely, typically falling in the range of a few seconds up to about 5 minutes. Preferably, exposure time to high intensity ultrasound will fall in the range of about 15 up to 60 seconds. Those skilled in the art recognize that the higher the acoustic power applied, the less exposure time to high intensity ultrasound is required, and vice versa.

The interfacial free energy is directly proportional to the polarity difference between the two liquids. Thus at a given operating temperature a minimum free energy at the interface between the two liquids is essential to form the desired polymer shell. Thus, if a homologous series of dispersing agents is taken with a gradual change in polarity, e.g., ethyl esters of alkanoic acids, then higher homologues are increasingly nonpolar, i.e., the interfacial tension between these dispersing agents and water increases as the number of carbon atoms in the ester increases. Thus it is found that, although ethyl acetate is water-immiscible (i.e., an ester of a 2 carbon acid), at room temperature (~20° C.), this dispersing agent alone will not give a significant yield of polymer shell-coated particles. In contrast, a higher ester such as ethyl octanoate (ester of an 8 carbon acid) gives polymer shell-coated particles in high yield. In fact, ethyl heptanoate (ester of a 7 carbon acid) gives a moderate yield while the lower esters (esters of 3, 4, 5, or 6 carbon acids) give poor yield. Thus, at a given temperature, one could set a condition of minimum aqueous-dispersing agent interfacial tension required for formation of high yields of polymer shell-coated particles.

Temperature is another variable that may be manipulated to affect the yield of polymer shell-coated particles. In general the surface tension of a liquid decreases with increasing temperature. The rate of change of surface tension with temperature is often different for different liquids. Thus, for example, the interfacial tension ($\Delta\gamma$) between two liquids may be $\Delta\gamma_1$ at temperature $T_1$ and $\Delta\gamma_2$ at temperature $T_2$. If $\Delta\gamma_1$ at $T_1$ is close to the minimum required to form polymeric shells of the present invention, and if $\Delta\gamma_2$ (at temp. $T_2$) is greater than $\Delta\gamma_1$, then a change of temperature from $T_1$ to $T_2$ will increase the yield of polymeric shells. This, in fact, is observed in the case of ethyl heptanoate, which gives a moderate yield at 20° C. but gives a high yield at 10° C.

Temperature also affects the vapor pressure of the liquids employed. The lower the temperature, the lower the total vapor pressure. The lower the total vapor pressure, the more efficient is the collapse of the cavitation bubble. A more efficient collapse of the ultrasonic irradiation bubble correlates with an increased rate of superoxide ($HO_2^-$) formation. Increased rate of superoxide formation leads to increased yields of polymeric shells at lower temperatures. As a countervailing consideration, however, the reaction rate for oxidation of sulfhydryl groups (i.e., to form disulfide linkages) by superoxide ions increases with increasing temperature. Thus for a given liquid subjected to ultrasonic irradiation conditions, there exists a fairly narrow range of optimum operating temperatures within which a high yield of polymeric shells is obtained.

Thus a combination of two effects, i.e., the change in surface tension with temperature (which directly affects the unfolding and/or conformational changes of the polymer) and the change in reaction yield (the reaction being crosslinking of the polymer via formation of disulfide linkages) with temperature dictate the overall conversion or yield of polymer shell-coated particles.

The ultrasonic irradiation process described above may be manipulated to produce polymer shells (containing imaging agents) having a range of sizes. Presently preferred particle radii fall in the range of about 0.1 up to about 5 micron. A narrow size distribution in this range is very suitable for intravenous drug delivery. The polymer shell-coated imaging agents are then suspended in an aqueous biocompatible liquid (as described above) prior to administration by suitable means.

Variations on the general theme of dissolved imaging agents enclosed within a polymeric shell are possible. A suspension of fine particles of imaging agents in a biocompatible dispersing agent could be used (in place of a biocompatible dispersing agent containing dissolved imaging agents) to produce a polymeric shell containing dispersing agent-suspended particles of imaging agent(s). In other words, the polymeric shell could contain a saturated solution of imaging agent in dispersing agent. Another variation is a polymeric shell containing a solid core of imaging agent produced by initially dissolving the imaging agent(s) in a volatile organic solvent (e.g. benzene), forming the polymeric shell and evaporating the volatile solvent under vacuum, e.g., in a rotary evaporator, or freeze-drying the entire suspension. This results in a structure having a solid core of imaging agent surrounded by a polymer coat. This latter method is particularly advantageous for delivering high doses of imaging agent(s) in a relatively small volume.

Variations in the polymeric shell are also possible. For example, a small amount of polyethylene glycol (PEG) containing sulfhydryl groups could be included with the polymer. Upon ultrasonic irradiation, the PEG is crosslinked into the polymer (e.g., albumin or other appropriate proteins) and forms a component of the polymeric shell. A second approach would be to chemically attach the PEG to the protein prior to synthesis of polymeric shells therefrom. Alternatively, PEG can be linked to the polymer shell after preparation. All three synthetic schemes will introduce PEG to the protein polymeric shell.

Chemical methods to attach PEG into proteins are well established and include the use of PEG-cyanuric acids, as described in greater detail in the examples which follow. An alternative method includes the use of PEG-succinimidyl succinate derivatives which will react with the protein amine groups (Abuchowski et al., *Cancer Biochem. Biophys.* 7:175 (1984); Joppich, M. and Luisi, P. L., *Macromol. Chem.* 180:1381 (1979); Klibanov et al., *FEBS Letters* 268:235 (1990)). Yet another method involves use of a PEG-oxycarbonylimidazole derivative, which produces a stable urethane bond upon reaction with the protein amine group. (Beauchamp et al., *Anal. Biochem.* 131:25 (1983); Allen et al. *Biochem. Biophys. Acta* 1066:29 (1991)). Similarly, a PEG-tosylate derivative will also react with the protein amine groups (Nilsson, K. and Mosbach, K., *Methods in Enzymology* 104:56 (1984); Yoshinga et al., *J. Bioactive Comp. Polym.* 4:17 (1989)). Finally a PEG-aldehyde derivative will also react with the protein amine groups. A subsequent reduction step affords the desired protein-PEG conjugate.

PEG is known for its nonadhesive character and has been attached to proteins and enzymes to increase their circulation time in vivo (Abuchowski et al., *J. Biol. Chem.* 252:3578 (1977)). PEG has also been attached to phospholipids forming the lipidic bilayer in liposomes to reduce their uptake and prolong lifetimes in vivo (Klibanov et al., *FEBS Letters* 2.68:235 (1990)). Thus the incorporation of PEG into the walls of crosslinked protein shells alters their blood circulation time. This property can be exploited to maintain higher blood levels of the fluorine-containing compounds and prolonged release times thereof.

Of particular interest for application to vascular imaging are fluorocarbon-containing polymeric shells having prolonged circulation times. Currently used angiography techniques utilize X-ray contrast media and are invasive procedures. The potential of $^1$H-MRI has been recently demonstrated for angiography applications (Edelman and Warach, *New England J. of Medicine* 328:785–791 (1993)). Similarly, $^{19}$F-MRI or proton MRI is useful for angiography, with a number of advantages, such as the ability to achieve high contrast with reference to surrounding tissue (which does not contain any native fluorine). Examples of applications of such methodology include the diagnosis and identification of intracranial aneurysms, arteriovenous malformations, occlusions of the superior vena cava, inferior vena cava, portal vein, pelvic vein, renal vein, renal mesenteric artery, peripheral mesenteric artery, and the like.

Those of skill in the art will recognize that several variations are possible within the scope and spirit of this invention. For example, the dispersing agent within the polymeric shell may be varied, other natural and synthetic polymers may be used in the formation of the walls of the polymeric shell, and the like.

Moreover, polymeric shells of the present invention can be modified with a variety of reagents in addition to PEG. For example, the polymeric shell can optionally be modified by a suitable agent, wherein the suitable agent is associated with the polymeric shell through an optional covalent bond. Covalent bonds contemplated for such linkages include ester bonds, ether bonds, amide bonds, secondary amine or tertiary amine bonds, phosphate ester bonds, urethane bonds, diester bonds, sulfate ester bonds, and the like. Suitable agents contemplated for this optional modification of the polymeric shell include synthetic polymers (linear or branched polyalkylene glycols (as discussed above with PEG), polyvinyl alcohol, polyhydroxyethyl methacrylate, polyacrylic acid, polyethyloxazoline, polyacrylamide, polyvinyl pyrrolidinone, and the like) phospholipid (such as phosphatidyl choline (PC), sphingomyelin, and the like), proteins (such as enzymes, antibodies, and the like), polysaccharides (such as starch, pectin, cellulose, dextrans, alginates, chitosan, hyaluronic acid, and the like), chemical modifying agents (such as pyridoxal-5-phosphate, analogs of pyridoxal, dialdehydes, diasiprin esters, and the like), or combinations of any two or more thereof.

Besides modifying the surface for increased circulation times such as with PEG, the polymeric shell can be modified to have desired organ and cellular selectivity. For example ligands such as sugars and small carbohydrates (e.g., galactose) can be attached, the resulting polymeric shells will subsequently be recognized in vivo by oligosaccharide receptors (e.g., asiologlycoprotein receptor). Besides targeting oligosaccharide receptors, ligands can be attached to the polymeric shell that recognize steroid receptors, protein & polypeptide receptors, and neurotransmitter receptors. Attachment of antibodies is also contemplated. By coupling specific antibodies for specific cellular receptors, polymeric shells of the invention can be directed to a wealth of well known receptors. Besides natural ligands for biological receptors, synthetic ligands that mimic biological receptors are also suitable.

According to the present invention, imaging agents are contained within a shell having a cross-sectional diameter of no greater than about 100 microns (as used herein, the term "micron" refers to a unit of measure of one one-thousandth of a millimeter). Typically, cross-sectional diameters of invention polymeric shells fall in the range of about 0.001 up to 100 microns, with cross-sectional diameters in the range of about 0.1 up to 10 microns being presently preferred. A cross-sectional diameter of less than about 5 microns is especially preferred, while a cross-sectional diameter of less than about 1 micron is presently most preferred for the intravenous route of administration.

Contrast agents of the present invention may be introduced into the body space in various ways depending on the imaging requirements. For example, aqueous liquid suspensions may be placed in the gastrointestinal tract by oral ingestion or suppository (e.g., to obtain images of the stomach and gastrointestinal tract), inserted by a syringe into non-vascular spaces such as the cerebro-spinal cavity, or injected into the vascular system generally or into the vessels of a specific organ such as the coronary artery. In addition, contrast agents of the invention can also be injected into other body spaces such as the anterior and posterior eye spaces, the ear, the urinary bladder (e.g., by way of the urethra), the peritoneal cavities, ureter, urethra, renal pelvis, joint spaces of the bone, lymphatic vessels, the subarachnoid spaces, the ventricular cavities, and the like.

The polymeric shell containing solid or liquid cores of imaging agent allows for the directed delivery of high doses of imaging agent in relatively small volumes. This minimizes patient discomfort at receiving large volumes of fluid.

The invention will now be described in greater detail by reference to the following non-limiting examples.

EXAMPLE 1

Synthesis of Dodecafluorononane ($C_9F_{20}$) Entrapped within a Polymeric Shell A 20 mL glass reaction cell, titanium horn and collar were washed with alcohol and sterile saline prior to synthesis as was all equipment used. In a typical reaction, 3.5 mL of sterile 5% w/v USP (United States Pharmacopaeia) human serum albumin (Alpha Therapeutics Corporation) was added to a reaction cell and the cell attached to the ultrasonic horn (Heat Systems XL2020, 20 KHz, 400 W maximum power). The horn and cell were then submerged in a temperature control bath set to 22° C. Reactions run at 22° C. appeared to be optimum, however the product can be synthesized over a wide range of temperatures (0° up to about 40° C.). Temperature control is critical to high yields of material, and the optimum temperature depends on the specific experimental configuration.

Six milliliters of dodecafluorononane ($C_9F_{20}$) was next added, and the ultrasonic source turned on at a power setting of 7. The amount of fluorocarbon added can be varied from less than 1 mL up to about 13 mL with good yield of protein polymeric shells. The reaction is complete in about 30 seconds. Yields at shorter and longer reaction times appear to be less than optimal. The homogeneous suspension produced contains the entrapped dodecafluorononane in protein polymeric shells and is approximately 60% perfluorononane by volume. The aqueous suspension may then be stored in a sterile container at 4° C.

A typical reaction yields a solution that contains approximately $1 \times 10^9$ shells per mL with an average shell diameter of 2 microns with a standard deviation of 1 micron. This synthetic procedure is seen to yield high concentrations of the micron-sized biomaterial with narrow size distributions.

EXAMPLE 2

Synthesis of Perfluorotributyl Amine ($C_{12}F_{27}N$) or Perfluorotripropyl Amine ($C_9F_{21}N$) Entrapped within Polymeric Shells The 5% w/v USP human serum albumin (3.5 mL) and fluoroamine (6 mL) were added to a glass reaction cell and irradiated with high intensity ultrasound. The reaction conditions were a power setting of 7, a bath temperature of 22° C. and a reaction time of approximately 30 seconds. Once again a higher concentration of both perfluorotripropyl amine [$(C_3F_7)_3N$] and perfluorotributyl amine [$(C_4F_9)_3N$] entrapped in a protein polymeric shell are synthesized ($1 \times 10^9$ shells/mL) with an average diameter of 2 microns.

EXAMPLE 3

Synthesis of Perfluorodecalin ($C_{10}F_{18}$) Entrapped within a Polymeric Shell The 5% w/v USP human serum albumin (3.5 mL) and perfluorodecalin ($C_{10}F_{18}$; 6 mL) were added to a glass reaction cell and irradiated with high intensity ultrasound. The reaction conditions were a power setting of 7, a bath temperature of 22° C. and a reaction time of approximately 30 seconds. High concentrations with narrow size distributions of perfluorodecalin contained within a protein polymeric shell were synthesized. Furthermore, since perfluorodecalin and perfluorotripropylamine are the major constituents of the FDA approved fluorocarbon, Fluosol DA, the medicinal use of these compounds in medical imaging should be readily accepted by regulatory authorities.

EXAMPLE 4

Synthesis of Perfluoro 15-crown-5 ($C_{10}F_{20}O_5$) Entrapped within a Polymeric Shell The 5% w/v USP human serum albumin (3.5 mL) and the fluorocrown ether ($C_{10}F_2O_5$; 6 mL) were added to a glass reaction cell and irradiated with high intensity ultrasound. The reaction conditions were a power setting of 7, a bath temperature of 22° C. and a reaction time of approximately 30 seconds. As before, high concentrations of fluorocrown ether contained in a protein polymeric shell with narrow size distributions are synthesized. In fact this experimental procedure to synthesize fluorocarbon filled polymeric shells was typical for all of the fluorocarbons investigated.

EXAMPLE 5

Synthesis of Perfluoro-t-butylbutene ($C_{10}F_8H_2$) Entrapped within a Polymeric Shell The 5% w/v USP human serum albumin (3.5 mL) and $C_{10}F_{18}H_2$ (6 mL) can be added to a glass reaction cell and irradiated with high intensity ultrasound. Reaction conditions comprising a power setting of 7, a bath temperature of 22° C. and a reaction time of approximately 30 seconds would typically be employed. By this procedure, protein polymeric shell having a high concentration of fluoro-t-butylbutane entrapped therein could be synthesized.

EXAMPLE 6

Synthesis of Saline Entrapped within Gluten Polymeric Shells

A 20 mL glass reaction cell, titanium horn and collar were washed with alcohol and sterile saline prior to synthesis as was all equipment used. In a typical reaction, 3.5 mL of 2% w/v gluten (Sigma) in soybean oil and 4 mL of saline were added to a reaction cell and the cell attached to the ultrasonic horn (Heat Systems XL2020, 20 KHz, 400 W maximum power). The amount of saline or water added can be varied from less than 1 mL to more than 10 mL. The horn and cell were then submerged in a temperature controlled bath set to 25° C. Reactions run at 25° C. appeared to be optimum, although the products can be synthesized over a wide range of temperatures (0° to 40° C.). Temperature control is critical to high yields of material, and the optimum temperature depends on the specific experimental configuration. The ultrasonic source is turned on at a power setting of 7. The reaction is complete in about 30 seconds. Yields at shorter and longer reaction times appear to be less than optimal. The homogeneous suspension produced contains the entrapped saline in gluten polymeric shells and is approximately 60% encapsulated saline by volume. Any excess oil and gluten is washed away from the polymeric shells and the remaining saline filled polymeric shells are suspended in saline. The aqueous suspension may then be stored in a sterile container at 4° C.

A typical reaction yields a solution that contains approximately $1\times10^9$ polymeric shells per mL with an average shell diameter of 3.5 microns with a standard deviation of 1 micron. This synthetic procedure yields high concentrations of micron-sized biomaterial with narrow size distributions.

EXAMPLE 7

Preparation of PEG Linked to Albumin Polymeric Shells Containing Dodecafluorononane 5% w/v USP human serum albumin and dodecafluorononane were added to a glass reaction cell and irradiated with high intensity ultrasound (as described in great detail in Example 1). The reaction conditions were a power setting of 7, a bath temperature of 22° C. and a reaction time of approximately 30 seconds. Once again high concentrations of dodecafluorononane entrapped in protein polymeric shells are synthesized ($1\times10^9$ shells/mL) with an average diameter of 2 microns. After synthesis the polymeric shells containing perfluorononane were filtered using a centricom filter (300,000 MW cut-off).

PEG (10,000 MW) is attached to the albumin polymeric shell using cyanuric trichloride. Cyanuric trichloride first reacts with the PEG hydroxyl group. This conjugate then reacts with the amine groups on the albumin to produce the desired product. The extent of PEG-ylation can be determined using 2,4,6-trinitrobenzenesulfonic acid. Monitoring the absorption in the visible range (@340 nm) shows greater than 90% PEG-ylation of the protein polymeric shell.

EXAMPLE 8

Preparation of Hemoglobin Polymeric Shells

A 20 mL glass reaction cell, titanium horn and collar were washed with alcohol and sterile saline prior to synthesis as was all equipment used. In a typical reaction, 3.5 mL of 5% w/v hemoglobin (human or bovine) was added to a reaction cell which was attached to the ultrasonic horn (Heat Systems XL2020, 20 KHz, 400 W maximum power). The horn and cell were then submerged in a temperature controlled bath set to 55° C. Reactions run at 55° C. appeared to be optimum, however the product can be synthesized over a wide range of temperatures (0° to 80° C.). The pH was 6.8. Temperature control is critical to high yields of material, and the optimum temperature depends on the specific experimental configuration. The ultrasonic source was turned on at a power setting of 7; the manufacturer's nomograph suggests a power output of approximately 150 W/cm². The reaction is complete in about 30 seconds. Yields at shorter and longer reaction times appear to be less optimal. For bovine Hb, the 2.5% w/v solution was passed through a Sephadex G-25 gel column to remove any anions such as phosphates. In a typical synthesis of Hb polymeric shells, the ultrasonic horn was positioned at the air-water interface. The homogeneous suspension produced contains proteinaceous red blood cells. The aqueous suspension may then be stored in a sterile container at 4° C.

A typical reaction yields a solution that contains approximately $3\times10^8$ shells per mL with an average shell diameter of 3 microns with a standard deviation of 1 micron. This synthetic procedure yields high concentrations of micron-sized biomaterial with narrow size distributions.

After synthesis, the hemoglobin polymeric shells remain as a suspension in the native protein solution. To separate the hemoglobin polymeric shells from the unreacted protein, several methods were used: filtration, centrifugation and dialysis. The first method included filtering the mixture through an Anotop syringe filter with 0.2 μm diameter pore size (Whatman, Inc.). The filter was washed with several volumes of water until the filtrate contained very little or no protein (as determined by UV-Visible spectroscopy). The hemoglobin polymeric shells were "backwashed" out of the filter and resuspended in an equivalent volume of water. The second purification procedure involved the use of a Centricom centrifuge filter with a molecular-weight cut-off of 100 kilodaltons(kD). The centrifuge filter is a centrifuge tube separated by a filtration membrane in the middle. Centrifugation of the hemoglobin polymeric shell solution at 1000 G for 5 minutes allowed most of the native and denatured Hb (64.5 kD) to pass through the membrane. Finally, dialysis with a large molecular weight (300 kD) membrane was also used to purify the hemoglobin polymeric shells. However, this method required approximately 2 days of dialysis. The presently preferred method for the purification of the hemoglobin polymeric shells is with the Centricom centrifuge filter.

EXAMPLE 9

Preparation of Hemoglobin Polymeric Shells Containing Dodecafluorononane

A 20 mL glass reaction cell, titanium horn and collar were washed with alcohol and sterile saline prior to synthesis as was all equipment used. In a typical reaction, 3.5 mL of 5% w/v hemoglobin (human or bovine) and 5 mL of dodecafluorononane were added to a reaction cell which was attached to the ultrasonic horn (Heat Systems XL2020, 20 KHz, 400 W maximum power). The horn and cell were then submerged in a temperature controlled bath set to 20° C. Reactions run at 20° C. appeared to be optimum, however the product can be synthesized over a wide range of temperatures (0° to 80° C.). The pH was 6.8. Temperature control is critical to high yields of material, and the optimum temperature depends on the specific experimental configuration. The ultrasonic source was turned on at a power setting of 7; the manufacturer's nomograph suggests a power output of approximately 150 W/cm$^2$. The reaction is complete in about 30 seconds. Yields at shorter and longer reaction times appear to be less than optimum. For bovine Hb, the 2.5% w/v solution was passed through a Sephadex G-25 gel permeation column to remove any anions such as phosphates. In a typical synthesis of Hb polymeric shells, the ultrasonic horn was positioned at the Hb-dodecafluorononane interface. The homogeneous suspension produced contains polymeric shells composed of hemoglobin containing dodecafluorononane. The aqueous suspension may then be stored in a sterile container at 4° C.

A typical reaction yields a solution that contains approximately $3 \times 10^8$ shells per mL with an average shell diameter of 3 microns with a standard deviation of 1 micron. This synthetic procedure yields high concentrations of micron-sized biomaterial with narrow size distributions.

After the synthesis, the polymeric shells composed of hemoglobin containing dodecafluorononane remain as a suspension in the native protein solution. To separate the polymeric shells from the unreacted protein, several methods were used: filtration, centrifugation and dialysis. The first method included filtering the mixture through an Anotop syringe filter with 0.2 μm diameter pore size (Whatman, Inc.). The filter was washed with several volumes of water until the filtrate contained very little or no protein (as determined by UV-visible spectroscopy). The polymeric shells were "backwashed" out of the filter and resuspended in an equivalent volume of water. The second purification procedure involved the use of a Centricom centrifuge filter with a molecular-weight cut-off of 100 kilodaltons (kD). The centrifuge filter is a centrifuge tube separated by a filtration membrane in the middle. Centrifugation of the hemoglobin polymeric shells solution at 1000 G for 5 minutes allowed most of the native and denatured Hb (64.5 kD) to pass through the membrane. Finally, dialysis with a large molecular weight (300 kD) membrane was also used to purify the polymeric shells. However, this method required approximately 2 days of dialysis. The presently preferred method for purification of the polymeric shells is with the Centricom centrifuge filter.

EXAMPLE 10

Preparation of a Hemoglobin-Albumin Polymeric Shells

A 20 mL glass reaction cell, titanium horn and collar were washed with alcohol and sterile saline prior to synthesis as was all equipment used. In a typical reaction, 3.5 mL of a 5% w/v of 1:1 hemoglobin and albumin (human or bovine; hemoglobin/albumin ratio was varied from 0.1% to 99.9%) was added to a reaction cell which was attached to the ultrasonic horn (Heat Systems XL2020, 20 KHz, 400 W maximum power). The horn and cell were then submerged in a temperature controlled bath set to 55° C. Reactions run at 55° C. appeared to be optimum, however the product can be synthesized over a wide range of temperatures (0° to 80° C.). The pH was 6.8. Temperature control is critical to high yields of material, and the optimum temperature depends on the specific experimental configuration. The ultrasonic source was turned on at a power setting of 7; the manufacturer's nomograph suggests a power output of approximately 150 W/cm$^2$. The reaction is complete in about 30 seconds. Yields at shorter and longer reaction times appear to be less optimal. The homogeneous suspension produced contains the polymeric shell composed of both hemoglobin and human serum albumin. The aqueous suspension may then be stored in a sterile container at 4° C.

Again as described above, a typical reaction yields a solution that contains roughly $10^8$ shells per mL with an average shell diameter of 3 microns with a standard deviation of 1 micron. This synthetic procedure yields high concentrations of micron-sized biomaterial with narrow size distributions.

EXAMPLE 11

Preparation of a Hemoglobin-Albumin Polymeric Shells Containing Dodecafluorononane A 20 mL glass reaction cell, titanium horn and collar were washed with alcohol and sterile saline prior to synthesis as was all equipment used. In a typical reaction, 3.5 mL of a 5% w/v of 1:1 hemoglobin and albumin (human or bovine; hemoglobin/albumin ratio was varied from 0.1% to 99.9%) and 5 mL of dodecafluorononane were added to a reaction cell which was attached to the ultrasonic horn (Heat Systems XL2020, 20 KHz, 400 W maximum power). The horn and cell were then submerged in a temperature controlled bath set to 20° C. Reactions run at 20° C. appeared to be optimum, however the product can be synthesized over a wide range of temperatures (0° to 80° C.). The pH was 6.8. Temperature control is critical to high yields of material, and the optimum temperature depends on the specific experimental configuration. The ultrasonic source was turned on at a power setting of 7; the manufactures nomograph suggest a power output of approximately 150 W/cm$^2$. The reaction is complete in about 30 seconds. Yields at shorter and longer reaction times appear to be less optimal. The homogeneous suspension produced contains polymeric shells composed of hemoglobin and HSA containing perfluorononane. The aqueous suspension may then be stored in a sterile container at 4° C.

Again as described above, a typical reaction yields a solution that contains roughly $10^8$ shells per mL with an average shell diameter of 3 microns with a standard deviation of 1 micron. This synthetic procedure yields high concentrations of micron-sized biomaterial with narrow size distributions.

EXAMPLE 12

Preparation of PEG-linked to Hemoglobin Polymeric Shells

Polyethylene glycol (PEG) is known to be nontoxic, noninflammatory, nonadhesive to cells, and in general biologically inert. Proteins that are attached with PEG have been found to be less antigenic. With liposomes, circulation was found to increase upon binding/incorporation of PEG. Thus, incorporation of PEG into the polymeric shells of the invention will be expected to increase circulation time.

PEG (10,000 MW) is attached to the hemoglobin polymeric shells (prepared as described in Example 8) using cyanuric trichloride. Cyanuric trichloride first reacts with the PEG hydroxyl group. This conjugate then reacts with the amine groups on the albumin to produce the desired product. The extent of PEG-ylation can be determined using 2,4,6-trinitrobenzenesulfonic acid. Monitoring the absorption in the visible range (@ 340 nm) shows greater than 90% PEG-ylation of the protein polymeric shell.

EXAMPLE 13

Preparation of Hemoglobin Polymeric Shells Modified with PEG

As a further variation of the PEG-ylation described in Example 12, it has been found that by varying the concentration of PEG-thiol added to the protein (e.g., hemoglobin), it is possible to prepare PEG-hemoglobin polymeric shells that have varying stabilities. The PEG-thiol was prepared by techniques in the literature (such as Haris and Herati, *Polymer Preprints* 32:154 (1991)).

PEG-thiol of molecular weight 2000 g/mol was dissolved at a concentration of 1% (0.1 g added to 10 mL) in a 5% hemoglobin solution. The protein-PEG solution was irradiated with ultrasound to form a polymeric shell composed of hemoglobin and PEG.

EXAMPLE 14

Synthesis of Perfluorodecalin Entrapped within Albumin Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the perfluorodecalin, human serum albumin (5% w/v), and air are pumped into the reaction cell (via Ismatec peristaltic pump; calibration-speed setting:mL; 3:0.15 mL, 8:0.5 mL, 12:1.0 mL), where the ultrasonic event occurs with polymeric shell formation. Alternately, the perfluorodecalin and human serum albumin can be pumped into the reaction cell. Prior oxygenation of the HSA and/or pumping a separate line of air or oxygen into the reaction cell will help to optimize the synthesis of the polymeric shells. A single outlet approximately 3 cm above the inlet allows for the desired polymeric shells to be collected after ultrasonic processing. The reaction cell, teflon tubes, and ultrasonic horn can be autoclaved or washed with alcohol and sterile saline prior to synthesis.

The ultrasonic horn and cell were submerged in a temperature controlled bath set to 22° C. In a typical reaction, sterile 5% w/v USP (United States Pharmacopeia) human serum albumin (Alpha Therapeutics Corporation) and perfluorodecalin (PCR Chemicals) were pumped into the reaction cell. Reaction conditions and results are summarized in the following Table.

| Power Setting | Bath Temp., °C. | Res. Time (min.) | Norm. Conc. | Size, (micron) |
| --- | --- | --- | --- | --- |
| 7 | 25 | 0.5 | 1 | <1 |
| 7 | 25 | 1.0 | 3 | 1.2 |
| 7 | 35 | 1.0 | 2 | 1.5–2.0 |

As shown above, the optimal reaction conditions were a power setting of 7, bath temperature of 25° C., and a resident time of 1 minute (where resident time is defined as the reaction vol (0.47mL)/ flow rate (mL/min)). Polymeric shells containing perfluorodecalin can be synthesized over a wide range of temperatures (020 to 40° C.), power settings, and ultrasonic resident times. Temperature control and ultrasonic resident time appear to be the most critical parameters for synthesizing high yields of material, however, the optimum conditions depend on the specific experimental configuration in use. The homogeneous suspension produced contains the entrapped perfluorodecalin in protein polymeric shells and is approximately 60% perfluorodecalin by volume. The aqueous suspension may then be stored in a sterile container at 4° C.

A typical reaction yields a solution that contains approximately $1 \times 10^8$ to $1 \times 10^{10}$ polymeric shells per mL with an average shell diameter of 2 microns with a standard deviation of 1 micron. This synthetic procedure yields high concentrations of micron-sized biomaterial with narrow size distributions.

EXAMPLE 15

Synthesis of Perfluorooctylbromide Entrapped Within Albumin Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the perfluorooctylbromide, human serum albumin (5% w/v), and air are pumped (via peristaltic pump; Ismatec) into the cell where the ultrasonic event occurs with polymeric shell formation. Alternately, the perfluorodecalin and human serum albumin can be pumped into the reaction cell. Prior oxygenation of the HSA and/or pumping a separate line of air or oxygen into the reaction cell will help to optimize the synthesis of the polymeric shells. A single outlet approximately 3 cm above the inlet allows for the desired polymeric shells to be collected after ultrasonic processing. The reaction cell, teflon tubes, ultrasonic horn can be autoclaved or washed with alcohol and sterile saline prior to use.

The ultrasonic horn and cell were submerged in a temperature controlled bath set to 22° C. In a typical reaction, sterile 5% w/v USP human serum albumin (Alpha Therapeutics Corporation) and perfluorooctylbromide (PCR Chemicals) were pumped into the reaction cell. Reaction conditions and results are summarized in the following Table.

| Power Setting | Bath Temp., °C. | Res. Time (min.) | Norm. Conc. | Size, (micron) |
| --- | --- | --- | --- | --- |
| 7 | 25 | 0.5 | 1 | <1 |
| 7 | 25 | 1.0 | 3 | 1.5 |
| 7 | 35 | 1.0 | 1.5 | 1.5–2.0 |

As shown above, the optimal reaction conditions were a power setting of 7, bath temperature of 25° C., and a resident time of 1 minute. Polymeric shells containing perfluorooctylbromide can be synthesized over a wide range of temperatures (0° to 40° C.), power settings, and ultrasonic resident times. Temperature control and ultrasonic resident time appear to be the most critical parameters for synthesizing high yields of material, however, the optimum conditions depend on the specific experimental configuration in use. The homogeneous suspension produced contains the entrapped perfluorooctylbromide in protein polymeric shells and is approximately 60% perfluorooctylbromide by volume. The aqueous suspension may then be stored in a sterile container at 4° C.

A typical reaction yields a solution that contains approximately $1 \times 10^8$ to $1 \times 10^{10}$ polymeric shells per mL with an average shell diameter of 2 microns with a standard deviation of 1 micron. This synthetic procedure yields high concentrations of micron-sized biomaterial with narrow size distributions.

EXAMPLE 16

Synthesis of Hemoglobin Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the human hemoglobin (5% w/v), and air are pumped (via peristaltic pump; Ismatec) into the cell where the ultrasonic event occurs with polymeric shell formation. Alternately, a single line containing hemoglobin that was previously oxygenated can be pumped into the reaction cell. Prior oxygenation of the Hb and/or pumping a separate line of air or oxygen into the reaction cell will help to optimize the synthesis of the polymeric shells. A single outlet approximately 3 cm above the inlet allows for the desired polymeric shells to be collected after ultrasonic processing. The reaction cell, teflon tubes, and ultrasonic horn can be autoclaved or washed with alcohol and sterile saline prior to synthesis.

The ultrasonic horn and cell were submerged in a temperature control bath set to 22° C. In a typical reaction, sterile 5% w/v human hemoglobin (Sigma) was pumped into the reaction cell. Reaction conditions and results are summarized in the following Table.

| Power Setting | Bath Temp., °C. | Res. Time (min.) | Norm. Conc. | Size, (micron) |
| --- | --- | --- | --- | --- |
| 9 | 55 | 3 | 3 | 1 |
| 7 | 55 | 0.5 | — | — |
| 7 | 55 | 1.0 | 3 | 1.0 |
| 7 | 55 | 2.0 | 3 | 1.0 |
| 7 | 55 | 3.0 | 2.5 | 1.0 |
| 5 | 55 | 3.0 | 2 | 1.0 |

As shown above, the optimal reaction conditions were a power setting of 7, bath temperature of 55° C., and a resident time of 3 minutes. Hemoglobin polymeric shells can be synthesized over a wide range of temperatures (20° to 80° C.), power settings, and ultrasonic resident times. Temperature control and ultrasonic resident time appear to be the most critical parameters for synthesizing high yields of material, however, the optimum conditions depend on the specific experimental configuration in use. The homogeneous suspension produced contains the hemoglobin polymeric shells containing air. The aqueous suspension may then be stored in a sterile container at 4° C.

In a similar manner, hemoglobin polymeric shells containing perfluorocarbons can be synthesized.

A typical reaction yields a solution that contains approximately $1 \times 10^8$ to $1 \times 10^{10}$ polymeric shells per mL with an average shell diameter of 2 microns with a standard deviation of 1 micron. This synthetic procedure yields high concentrations of micron-sized biomaterial with narrow size distributions.

EXAMPLE 17

Synthesis of Gluten Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the gluten (5% w/v in soybean oil), and air are pumped (via peristaltic pump; Ismatec) into the cell where the ultrasonic event occurs with polymeric shell formation. Alternately, the gluten can be pumped into the reaction cell. Prior oxygenation of the gluten and/or pumping a separate line of air or oxygen into the reaction cell will help to optimize the synthesis of the polymeric shells. A single outlet approximately 3 cm above the inlet allows for the desired polymeric shells to be collected after ultrasonic processing. The reaction cell, teflon tubes, and ultrasonic horn can be autoclaved or washed with alcohol and sterile saline prior to use.

The ultrasonic horn and cell were submerged in a temperature controlled bath set to 22° C. In a typical reaction, 2% w/v gluten (Sigma Corporation) in soybean oil was pumped into the reaction cell. Reaction conditions and results are summarized in the following Table.

| Power Setting | Bath Temp., °C. | Res. Time (min.) | Norm. Conc. | Size, (micron) |
| --- | --- | --- | --- | --- |
| 7 | 45 | 0.5 | — | — |
| 7 | 55 | 0.5 | — | — |
| 7 | 55 | 1.0 | 1 | 4.0 |
| 7 | 55 | 2.0 | 3 | 3.0 |
| 7 | 55 | 3.0 | 2.5 | 4.0 |

As shown above, the optimal reaction conditions were a power setting of 7, bath temperature of 55° C., and a resident time of 2 minutes. Gluten polymeric shells can be synthesized over a wide range of temperatures (20° to 70° C.), power settings, and ultrasonic resident times. Temperature control and ultrasonic resident time appear to be the most critical parameters for synthesizing high yields of material, however, the optimum conditions depend on the specific experimental configuration in use. The aqueous suspension may then be stored in a sterile container at 4° C.

EXAMPLE 18

Synthesis of Saline Entrapped within Gluten Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the saline, gluten (5% w/v in soybean oil), and air are pumped (via peristaltic pump; Ismatec) into the cell where the ultrasonic event occurs with polymeric shell formation. Alternately, the saline and gluten can be pumped into the reaction cell. Prior oxygenation of the gluten and/or pumping a separate line of air or oxygen into the reaction cell will help to optimize the synthesis of the polymeric shells. A single outlet approximately 3 cm above the inlet allows for the desired polymeric shells to be collected after ultrasonic processing. The reaction cell, teflon tubes, and ultrasonic horn can be autoclaved or washed with alcohol and sterile saline prior to use.

The ultrasonic horn and cell were submerged in a temperature controlled bath set to 22° C. In a typical reaction, 2% w/v Gluten (Sigma Corporation) in soybean oil and saline were pumped into the reaction cell. Reaction conditions and results are summarized in the following Table.

| Power Setting | Bath Temp., °C. | Res. Time (min.) | Norm. Conc. | Size, (micron) |
| --- | --- | --- | --- | --- |
| 7 | 25 | 0.5 | — | — |
| 7 | 25 | 1 | 1 | 3.5 |
| 7 | 25 | 2.0 | 3 | 3.0 |
| 7 | 25 | 3.0 | 2.5 | 2.5 |

As shown above, the optimal reaction conditions were a power setting of 7, bath temperature of 25° C. and a resident time of 2 minutes. Gluten polymeric shells containing saline can be synthesized over a wide range of temperatures (0° to 40° C.), power settings, and ultrasonic resident times. Temperature control and ultrasonic resident time appear to be the most critical parameters for synthesizing high yields of material, however, the optimum conditions depend on the specific experimental configuration in use. The homogeneous suspension produced contains the entrapped saline in protein polymeric shells and is approximately 60% by volume. The aqueous suspension may then be stored in a sterile container at 4° C.

A typical reaction yields a solution that contains approximately $1\times10^8$ to $1\times10^{10}$ polymeric shells per mL with an average shell diameter of 2 microns with a standard deviation of 1 micron. This synthetic procedure yields high concentrations of micron-sized biomaterial with narrow size distributions.

EXAMPLE 19 pH Effect on the Synthesis of Saline Entrapped within Gluten Polymeric Shells Using a Continuous Flow Ultrasonic Generator A small volume (0.47 mL) stainless steel reaction cell is attached (threaded fitting) to the titanium horn of a standard ultrasonic device (Heat Systems XL2020, 20 KHz, 400 W maximum power). The stainless steel reaction cell has an inlet open at the bottom where the saline, gluten (5% w/v in soybean oil), and air are pumped (via peristaltic pump; Ismatec) into the cell where the ultrasonic event occurs with polymeric shell formation. The pH of the solution was changed with HCl to determine the effect of pH on the synthesis of the polymeric shells. A single outlet approximately 3 cm above the inlet allows for the desired polymeric shells to be collected after ultrasonic processing. The reaction cell, teflon tubes, and ultrasonic horn can be autoclaved or washed with alcohol and sterile saline prior to use.

The ultrasonic horn and cell were submerged in a temperature control bath set to 22° C. In a typical reaction, 2% w/v Gluten (Sigma Corporation) in soybean oil and saline were pumped into the reaction cell. The reaction conditions were a power setting of 7, bath temperature of 25° C., and a resident time of 2 minutes. Reaction conditions and results are summarized in the following Table.

| pH | Norm. Conc. | Size (micron) |
| --- | --- | --- |
| 7 | 1 | 3 |
| 4 | 1 | 3 |
| 2 | 0.83 | 2.7 |
| 0.5 | 0.66 | 2.7 |

As shown above, gluten polymeric shells containing saline can be synthesized over a wide range of acidic conditions. The homogeneous suspension produced contains the entrapped saline in protein polymeric shells and is approximately 60% saline by volume. The aqueous suspension may then be stored in a sterile container at 4° C.

A typical reaction yields a solution that contains approximately $1\times10^8$ to $1\times10^{10}$ polymeric shells per mL with an average shell diameter of 2 microns with a standard deviation of 1 micron. This synthetic procedure yields high concentrations of micron-sized biomaterial with narrow size distributions.

EXAMPLE 20

Parameters Affecting Polymeric Shell Formation

Several variables such as protein concentration, temperature, ultrasonic irradiation time, concentration of pharmacologically active agent, and acoustic intensity were tested to optimize formation of polymeric shell. These parameters were determined for crosslinked bovine serum albumin shells containing toluene.

Polymeric shells made from solutions having protein concentrations of 1%, 2.5%, 5% and 10% were counted with the particle counter to determine a change in the size and number of polymeric shells produced. The size of the polymeric shells was found not to vary with protein concentration, but the number of polymeric shells per mL of "milky suspension" formed increased with the increase in concentration of the protein up to 5%. No significant change in the number of polymeric shells was found to occur above that concentration.

Initial vessel temperatures were found to be important for optimal preparation of polymeric shells. Typically, initial vessel temperatures were maintained between 0° C. and 45° C. The aqueous-oil interfacial tension of the oils used for formation of the polymeric shell was an important parameter, which also varied as a function of temperature. The concentration of pharmacologically active agent was found not to significantly affect the yield of protein shells. It is relatively unimportant if the pharmacologically active agent is incorporated in the dissolved state, or suspended in the dispersing medium.

Ultrasonic irradiation time was an important factor determining the number of polymeric shells produced per mL. It was found that an ultrasonic irradiation time greater than three minutes produced a decrease in the overall count of polymeric shells, indicating the possible destruction of polymeric shells due to excessive ultrasonic irradiation. Ultrasonic irradiation times less than three minutes were found to produce adequate numbers of polymeric shells.

According to the nomograph provided by the manufacturer of the sonicator, the acoustic power rating of the sonicator employed herein is approximately 150 Watts/cm$^2$. Three power settings in order of increasing power were used, and it was found that the maximum number of polymeric shells were produced at the highest power setting.

EXAMPLE 21

Parameters Affecting Preparation of Hemoglobin Polymeric Shells

Several variables such as protein concentration, temperature, sonication time, acoustic intensity and pH were tested to optimize formation of polymeric shells composed of hemoglobin.

These materials were prepared from 1%, 2.5%, 5%, and 10% hemoglobin solutions. They were also prepared from mixed protein solution such as hemoglobin and human serum albumin with concentrations again ranging from 1 to 10%. The size of the resulting polymeric shells and concentrations thereof were determined with a particle counter. The size was found not to significantly vary with starting protein concentration. The number prepared increased with increased starting protein concentration up to about 5%. No significant change in the number was found to occur above that starting concentration.

Initial vessel temperatures were found to be important for optimal preparation of polymeric shells composed of hemoglobin. Typically the initial reaction temperatures were maintained between 0° and 80° C. The optimal starting temperature was found to be about 55° C.

Sonication time was also found to be an important factor determining the number of polymeric shells produced per mL. It was found that a sonication time of approximately three minutes was good for synthesizing a high concentration of polymeric shells. Longer or shorter sonication times produced fewer (but still an adequate number of) polymeric shells composed of hemoglobin.

According to the nomograph provide by the manufacture of the sonicator, the acoustic power rating of the sonicator used in these experiments is approximately 150 Watts/cm$^2$. Other power settings were also found to produce a large number of polymeric shells composed of hemoglobin.

EXAMPLE 22

Preparation of Crosslinked PEG-walled Polymeric Shells

As an alternative to the use of thiol (sulfhydryl) containing proteins in the formation of, or as an additive to polymeric shells of the invention, a thiol-containing PEG was prepared. By varying the concentration of PEG-SH (i.e., PEG modified to contain sulfhydryl and/or disulfide end groups) added to the 5% albumin solution, it was possible to obtain protein polymeric shells with varying stabilities in vivo. Fluorocarbon-containing protein shells having prolonged circulation times in vivo were found to have particular benefit for imaging the vascular system. These shells remained within the circulation for extended periods, relative to shells not containing PEG in the shell walls. This allowed, for example, visulation of cardiac circulation, and provided a non-invasive means of evaluating the coronary circulation, instead of using conventional invasive techniques such as angiography. PEG-SH was prepared by techniques known in the art (such as the technique of Harris and Herati, as described in *Polymer Preprints* 32:154–155 (1991)).

PEG-SH of molecular weight 2000 g/mol was dissolved at a concentration of 1% (0.1 g added to 10 mL) in a 5% albumin solution. This protein/PEG solution was overlayered with oil as described in Example 2 and sonicated to produce oil-containing polymeric shells with walls comprising crosslinked protein and PEG.

Other synthetic water-soluble polymers that may be modified with thiol groups and utilized in lieu of PEG include, for example, polyvinyl alcohol, polyhydroxyethyl methacrylate, polyacrylic acid, polyethyloxazoline, polyacrylamide, polyvinyl pyrrolidinone, polysaccharides (such as chitosan, alginates, hyaluronic acid, dextrans, starch, pectin, etc), and the like.

EXAMPLE 23

Stability of Polymeric Shells

Suspensions of soybean oil entrapped in protein (human serum albumin-HSA) polymeric shells were analyzed over time at three different temperatures to determine long-term stability. These suspensions were synthesized in a similar manner as described in Examples 1 through 4 except instead of a fluorocarbon, soybean oil was used. The solution was diluted to 20% v/v based on encapsulated soybean oil and were counted over a 27 day period using an Elzone particle counter.

| | Vesicle Concentration in Saline (#/mL × 10$^{10}$) | | |
|---|---|---|---|
| Day | 4° C. | 25° C. | 38° C. |
| 0 | 7.9 | 8.9 | 8.1 |
| 1 | 7.4 | 6.9 | 6.8 |
| 7 | 7.3 | 8.3 | 5.0 |
| 9 | 7.8 | 8.1 | 5.8 |
| 17 | 7.8 | 8.3 | 6.1 |
| 23 | 6.9 | 7.8 | 7.4 |
| 27 | 7.2 | 8.8 | 7.1 |

As seen from the above concentration data, soybean oil entrapped in polymeric shells remained fairly constant over the 27 day period at all temperatures.

EXAMPLE 24

Toxicity of Fluorocarbons Contained within Polymeric Shells

Five rats were injected through a catherized jugular vein with 5 mL of a 20% v/v fluorocarbon suspension (perfluorononane contained in an HSA protein polymeric shell) over 10 minutes. Fluorocarbons in general are nontoxic due to the strong fluorine-carbon bonds; indeed, fluorocarbons have been successfully used as FDA approved artificial blood substitutes (Fluosol DA). The rats were euthanized at specific times and autopsied. Besides observing the general health of the rat, the liver, spleen, lungs and kidneys were carefully examined. Rats examined at 0.5, 2, 8 and 24 hours were all healthy with no inflamed tissues or organs. The fifth rat is still alive and healthy after 90 days. For comparison, the equivalent dose of FDA approved soybean oil in a rat is the $LD_{50}$ amount, further suggesting that fluorocarbons are nontoxic and safe.

EXAMPLE 25

Polymeric Shells Investigated by Circular Dichrosium

Polymeric shells were synthesized from human serum albumin as described in Example 1. The polymeric shells were separated from the remaining albumin by sequential centrifugation, filtration with an Amicon filter or simple filtration. Sequential filteration with an amicon provides the best sample, as determined by analysis of the resultant wash by UV-VIS (absorption at 280 nm). A dilute solution of the polymeric shells was placed in a JASCO CD instrument. The polymeric shell spectrum and the spectrum of natural albumin (no treatment with ultrasound) were essentially identical. Thus the structure of albumin which comprises the polymeric shell is unaltered and analogous to free/native albumin.

EXAMPLE 26

Stability of Albumin Polymeric Shells Containing Perfluorooctylbromide (PFOB) in Simulated Gastric Fluid, at pH of 2 and pH of 10

5% w/v USP human serum albumin and PFOB were added to a glass reaction cell and irradiated with high intensity ultrasound (as described in detail in Example 1). The reaction conditions were a power setting of 7, a bath temperature of 22° C. and a reaction time of approximately 30 seconds. Once again high concentration of PFOB entrapped in a protein polymeric shell are synthesized ($1 \times 10^9$ shells/mL) with an average diameter of 2 microns. After synthesis the polymeric shells containing PFOB were filtered using a Centricom filter (300,000 MW cut-off).

The polymeric shells containing PFOB were then suspended in a pH solution of 2 and 10. In both acidic and basic solutions, the polymeric shells are stable with essentially no change in total number over approximately 24 hours. Counting studies (Elzone) showed less than approximately 5% loss after 24 hours in simulated gastric fluid (2.0 g NaCl; 36 mg pepsin; 7.0 mL HCl; qs 1000 mL; pH 1.2).

EXAMPLE 27

Morphology of the Micron-sized Hemoglobin Polymeric Shells

The morphology of the polymeric shell composed of hemoglobin was determined using transmission electron microscopy (TEM). The polymeric shell composed of hemoglobin was fixed with glutaraldehyde, stained with osmium tetroxide and potassium ferrocyanate (to provide contrast in regions of high protein concentration), embedded in a low viscosity resin, and ultra-microtomed (slice thickness ≈75 nm). Since some shrinkage in the overall diameter and some shape distortion of the polymeric shells are expected during this process, the true diameter of the polymeric shell is best represented by the solution particle size distribution (3 microns; std. dev. 1), rather than direct measurements from the TEM micrograph. A closer look at the TEM micrograph shows three distinctive regions: a clear central region; a dark, thin layer; and a loosely attached, diffuse, speckled gray region. The dark, thin layer is the polymeric shell. It contains a high density of protein, and during staining procedure, develops the most contrast. The loosely attached, gray matter appears to be native protein that adheres to the polymeric shell during the fixation step in the sample preparation. Initial measurements from this and many other micrographs indicate the shell thickness of the Hb polymeric shell to be 25–35 nm. Hemoglobin is a roughly spherical protein (Stryer, L., *Biochemistry*, W. H. Freeman, New York (1988)) with a diameter of 5.5 nm. Thus, the protein shell is approximately 4 to 20 Hb molecules thick.

EXAMPLE 28

Stability of Hemoglobin Polymeric Shells

The polymeric shell composed of hemoglobin were prepared as described in the above examples and were tested for stability by particle counting. After 3 months the concentration of polymeric shells had decreased by only about 10%, and about 25–30% after 6 months.

EXAMPLE 29

In vivo Biodistribution as Determined by an Entrapped Fluorescent Probe

To determine the uptake and biodistribution of liquid entrapped within the protein polymeric shells after intravenous injection, a fluorescent dye, rubrene (Aldrich), was entrapped within the HSA protein polymeric shell and used as a marker. Rubrene/toluene contained within polymeric shells were synthesized in a manner as described in Example 1. The resulting orange suspension was diluted to a 20% v/v solution and 2 mL were injected into the tail vein of a rat over ten minutes. One animal was sacrificed one hour after injection and another at 24 hours. 100 micron frozen sections of lungs, liver, kidney, spleen and bone marrow were examined under the fluorescent microscope for the entrapped dye and released dye. At one hour, the majority of the particles appeared to be intact and located in the lungs and liver. At 24 hours, the dye was located in the liver, lungs, spleen, and bone marrow. A general staining of the tissue was also observed indicating that the shell wall had been digested and dye liberated.

EXAMPLE 30

$^{19}$F Nuclear Magnetic Resonance Spectroscopy of a Neat Fluorocarbon and a Fluorocarbon Entrapped within a Polymeric Shell NMR spectra of the fluorocarbons contained within a protein polymeric shell and neat fluorocarbons were obtained on a Bruker 500 MHz NMR instrument. The instrument was tuned for $^{19}$F at its resonance frequency of 470.56 MHz. A deuterium solvent was used for locking and all spectra were externally referenced to Freon ($CCl_3F$) at 0 ppm. Perfluorononane and $CDCl_3$ were placed in a 5 mm NMR tube. The spectrum of pure perfluorononane was obtained with two sets of sharp peaks, one at −87 ppm, and the second set of peaks at −127, −128, and −133 ppm.

A suspension of perfluorononane entrapped within HSA protein polymeric shells was resuspended in $D_2O$ and a similar NMR spectrum was obtained. Strong signals were obtained from the 20% v/v fluorocarbon suspension with peaks or resonances at −81, −121, −122 and −126 ppm. The entrapment of the fluorocarbon in the polymeric shell during ultrasonic irradiation resulted in no chemical or structural changes of the perfluorononane. For example, with $C_9F_{20}$ two separate resonance were observed: one corresponding to the $CF_3$ at approximately −80 ppm and the second set of resonances at approximately −125 ppm, corresponding to the $CF_2$ group.

EXAMPLE 31

$^{19}F$ Nuclear Magnetic Resonance Spectroscopy of Fluorocarbons to Measure Local Temperature Variable temperature NMR spectra of fluorocarbons were obtained on a Bruker 500 MHz NMR instrument. The instrument was tuned for $^{19}F$ at its resonance frequency of 470.56 MHz. A deuterium solvent ($d_6$-dimethyl sulfoxide [$d_6$-DMSO]) was used for locking and all spectra were externally referenced to freon ($CCl_3F$) at 0 ppm. Perfluorododecane, which has a melting point of 77° C., and $d_6$-DMSO were placed in a 5 mm NMR tube at room temperature. Fluorine spectra were collected at different temperatures and the linewidths were measured. Linewidth data at –81 ppm, as a function of temperature, are shown below:

| Linewidth @ –81 ppm (Hz) | Temperature (°C.) |
| --- | --- |
| 51.1 | 102 |
| 57.0 | 82 |
| 64.65 | 60 |

The broad spectrum at lower temperatures starts to sharpen as the temperature increases, resulting from the perfluorododecane undergoing its solid to liquid phase transition. The change is sharp and sudden with temperature, as expected for a pure material.

In order to broaden and lower the melting temperature, pentane was added (approximately 2% v/v) to the perfluorododecane. As was seen above, the broad spectra at lower temperatures sharpened as the perfluorododecane goes through its solid to liquid phase transition. Linewidth data as a function of temperature for the perfluorododecane/pentane mixture are shown below:

| Linewidth (Hz) | | Temperature (°C.) |
| --- | --- | --- |
| –82 ppm | –123.3 ppm | |
| 21.26 | 87.17 | 77 |
| 165.89 | 280.50 | 67 |
| 216.6 | 341.2 | 57 |
| 290.77 | 436.15 | 47 |
| 578.27 | 451.33 | 37 |
| 577.62 | 525.11 | 27 |

The resulting perfluorododecane/pentane mixture has a lower melting point that is broadened as expected. With this system, temperature measurements can be made in the range from 27° to 77° C. Thus, given a linewidth, it is possible to determine the local temperature.

An example of use of this technique to determine localized temperatures in vivo involves the injection of protein shells containing fluorocarbon mixtures (e.g., such as described above) with broad melting transitions having temperature-linewidth correlations (which can be empirically obtained). Such a formulation will localize within the liver or spleen and, in addition to serving as a $^{19}F$ MRI contrast agent, may simultaneously be utilized to determine locally variant temperatures within the organ (allowing the elucidation of the pathology of significant abnormalities within the tissues).

EXAMPLE 32

$^{19}F$ Magnetic Resonance Imaging of Phantoms

Two types of entrapped fluorocarbons contained in polymeric shells were used in this phantom study. Perfluorononane and perfluorotributyl amine contained within HSA protein polymeric shells were synthesized as described in Examples 1 and 2. The synthesized suspension of 60% fluorocarbon per volume was diluted with saline and 2 milliliters placed in polystyrene tubes. The polystyrene tubes were then placed in a commercially available Siemens 2T MRI instrument (10 cm $^{19}F$ coil) operating at 1.5 tesla. $^{19}F$ magnetic resonance images of the tubes were taken over a 5 minute period with an echo time (TE) of 10 milliseconds and a time of repetition (TR) of 300 seconds (256×256 matrix).

| Perflurononane Contained in Polymeric Shells | | |
| --- | --- | --- |
| Dilution | [conc], M | Image Clarity |
| 1 | 1.8 | excellent |
| 1/2 | 0.9 | excellent |
| 1/4 | 0.45 | good |
| 1/10 | 0.18 | good |
| 1/50 | 0.09 | good |
| 1/100 | 0.02 | marginal |

Good MR phantom images were observed even at low concentrations of perfluorononane entrapped within polymeric shells. Very similar data was observed with polymeric shells that contained perfuorotributyl amine. Only at high dilution (1/100; 0.02M) was the image of poor quality and resolution.

EXAMPLE 33

$^{19}F$ Magnetic Resonance Imaging of Liver and Spleen In Vitro 300 gram rats were injected with 2 mL of 20% v/v perfluorononane contained within an HSA protein polymeric shell suspension. At 2 hours and at 5 days, a rat was sacrificed and the liver, spleen, kidneys, and lungs were removed. The entire liver, for example, was then placed in a 4 tesla MRI instrument operating with a 10 cm $^{19}F$ coil. $^{19}F$ magnetic resonance images of the liver, spleen and kidney were obtained using a $T_1$ weighted sequence with a TR=1 second, a TE=20 milliseconds and a data matrix of 256×128 (i.e., 128 phase encoding steps, 16 signal averages).

$^{19}F$ MRI images of the liver showed regions of varying intensity which correlated to varying degrees of liver uptake of the polymeric shells. For example, a dark region corresponding to the portal vein was observed where one would not expect the presence of the perfluorononane-containing polymeric shells since most of the shells are concentrated intracellularly within the RES of the liver.

The average image intensity of the liver scan at two hours after injection was approximately 20–30% higher than that of a scan recorded 5 days after injection, indicating partial dissipation of the perfluorononane, possibly through breakdown of the polymeric shells. Overall, excellent quality images showing liver morphology were obtained, demonstrating the potential of this technique in the diagnosis and localization of abnormal pathology within the liver.

EXAMPLE 34

In Vivo $^{19}F$ Magnetic Resonance Imaging of Liver and Spleen

A 150 gram rat was injected with 2 mL of a 20% v/v perfluorononane ($C_9F_{20}$) contained within HSA polymeric shells over 10 minutes. The entire rat was then placed in a 4 tesla MRI instrument operating with a 10 cm $^{19}$F coil. The rat was anaesthetized with ketamine before collecting images. $^{19}$F magnetic resonance images of the entire rat, as well as individual organs such as the liver, spleen and kidney, were obtained using a $T_1$ weighted sequence with a TR=1 second, a TE=20 milliseconds, and a data matrix of 256×128 (i.e., 128 phase encoding steps, 16 signal averages).

Rats were imaged at 15 minutes, 2 hours, and 24 hours after injection of the perfluorononane-containing HSA protein polymeric shells. Overall, excellent quality images showing liver and spleen morphology were obtained, demonstrating the potential of this technique in the diagnosis and localization of abnormal pathology within the liver RES containing organs.

EXAMPLE 35

In vivo $^{19}$F Magnetic Resonance Imaging with PEG Modified Polymeric Shells Containing Dodecafluorononane A 300 gram rat was injected with 5 mL of a 20% v/v $C_9F_{20}$ contained within polymeric shells modified with PEG (as described in Example 7) over 10 minutes. The rat was next placed in a 15 cm coil (a Siemens 1.5 tesla MRI magnet). ATE of 10 milliseconds and TR of 300 seconds was used to collect the images (256×256 matrix). The rat was anaesthetized with ketamine before collecting data. The liver and spleen were easily imaged taking 5 millimeter slice thickness.

The blood circulation time was determined using three rats. Without PEG-ylation the circulation time is approximately 5 minutes. After PEG-ylation the circulation time increases to approximately 70 minutes.

EXAMPLE 36

Determination of Local Temperature using In Vivo $^{19}$F Magnetic Resonance Imaging A 300 gram rat is injected with 5 mL of a 20% v/v perfluorododecane/2% pentane (or perfluorononadecanoic acid and 1% cholesterol) contained within HSA polymeric shells over 10 minutes. The rat is then placed in a 15 cm coil (a Siemens 1.5 tesla MRI magnet). ATE of 10 milliseconds and TR of 300 seconds is used to collect the images (256×256 matrix). The rat is anaesthetized with ketamine before collecting data. The liver and spleen are imaged over 15 minutes taking a 5 millimeter slice thickness. Data are collected at room temperature and at approximately 37° C., by wrapping the subdued rat in a heating pad.

EXAMPLE 37

In Vivo Oxygen Determination Using $^{19}$F Magnetic Resonance Imaging

A 300 gram rat is injected with 5 mL of 20% v/v perfluorononane contained within HSA polymeric shells over 10 minutes. The rat is next placed in a 15 cm coil (a Siemens 1.5 tesla MRI magnet). A TE of 70 milliseconds and TR of 3 seconds is used to collect the images (256×256 matrix). The rat is placed in a restraining harness before collecting data. The rat is first put in an oxygen chamber to increase oxygen metabolism, and the linewidth and image are collected. The rat is next injected with ketamine, to reduce the consumption of oxygen, and again the linewidth and image are collected. The linewidth and the intensity of the image are observed to change, corresponding to the amount of dissolved oxygen in the rat. The largest linewidth is observed at higher oxygen concentrations. The liver and spleen are imaged over 15 minutes taking a 5 millimeter slice thickness. Two data sets are collected, one at room temperature and another at 37° C., by wrapping the anaesthetized rat in a heating pad.

EXAMPLE 38

Synthesis of Paramagnetic Cations Bound to Polyanions

Synthesis of Gd-alginates can be carried out, for example, by dispersing the alginate in a solution of $GdCl_3$. For example, small spherical particles of Gd-alginate suitable for intravascular injection may be synthesized by ultrasonic irradiation of a solution containing Gd ions (e.g., $GdCl_3$) and adding small quantities of Na-alginate solution. The alginate is dispersed into the solution of Gd ions by the ultrasonic irradiation, and crosslinked by the multivalent Gd ions, producing micron sized particles of Gd-alginate. Besides using ultrasonic irradiation, low or high speed mixing can also be used.

Alternatively, a solution of Na-alginate is overlaid or layered on an immiscible organic solvent or oil (e.g., soybean oil, sunflower oil, toluene, methylene chloride, chloroform, and the like). The liquids are subjected to ultrasonic irradiation whereby the alginate-containing aqueous phase is dispersed into the organic phase, and then a solution of multivalent ions (e.g., $GdCl_3$, $MnCl_3$, $FeCl_3$, etc.) is added. The Na-alginate is thereby crosslinked, producing tiny spherical particles of Gd-alginate which are suitable for use as an MRI contrast agent following intravascular injection. Essentially any synthetic technique using alginates and multivalent cations can be used to form spheres, fibers, plates, blocks and the like.

While the invention has been described in detail with reference to certain preferred embodiments thereof, it will be understood that modifications and variations are within the spirit and scope of that which is described and claimed.

That which is claimed is:

1. A composition for obtaining in vivo medical diagnostic images, said composition comprising non-fluorinated imaging agent(s) substantially completely contained within a polymeric shell;

wherein said polymeric shell comprises a biocompatible polymer which is substantially crosslinked by way of disulfide bonds, and wherein said crosslinked polymer is a naturally occurring polymer, wherein said polymer, prior to crosslinking, has covalently attached thereto sulfhydryl groups or disulfide groups wherein said disulfide bonds are crosslinked directly, that is, without a crosslinking agent being used.

2. A composition according to claim 1 wherein said polymeric shell further comprises polyethylene glycol covalently linked thereto.

3. A composition according to claim 1 wherein said composition is useful for the in vivo determination of local oxygen concentrations.

4. A composition according to claim 1 wherein said composition is capable of undergoing a phase transition.

5. A composition according to claim 4 wherein said composition is useful for imaging as well as in vivo temperature determination.

6. A composition according to claim 1 wherein said naturally occurring polymers are selected from proteins containing sulfhydryl groups and/or disulfide groups, polypeptides containing sulfhydryl groups and/or disulfide groups, lipids containing sulfhydryl groups and/or disulfide groups, polynucleic acids containing sulfhydryl groups and/or disulfide groups, or polysaccharides containing sulfhydryl groups and/or disulfide groups.

7. A composition according to claim 1 wherein the disulfide bonds on the crosslinked polymer are formed by ultrasonic irradiation.

8. A composition according to claim 1 wherein the disulfide bonds on the crosslinked polymer are formed by reaction with free radicals.

9. A composition according to claim 6 wherein said biocompatible polymer is albumin.

10. A composition according to claim 6 wherein said biocompatible naturally occurring polymer is hemoglobin.

11. A composition according to claim 6 wherein said biocompatible naturally occurring polymer is gluten.

12. A composition according to claim 6 wherein said biocompatible naturally occurring polymer is lipase.

13. A composition according to claim 1 wherein said imaging agent is selected from superparamagnetic or paramagnetic metal particles suspended in a biocompatible medium.

14. A composition according to claim 13 wherein said metal particle is iron, iron oxide, manganese or manganese oxide.

15. A composition according to claim 1 wherein said magnetic resonance imaging agent is selected from gadolinium, dysprosium, or manganese metal complexes that are encapsulated within the polymeric shell.

16. A composition according to claim 1 wherein said polymeric shell containing agent therein is suspended in a biocompatible aqueous liquid.

17. A composition according to claim 16 wherein said biocompatible aqueous liquid is selected from water, buffered aqueous media, saline, buffered saline, solutions of amino acids, solutions of sugars, solutions of vitamins, solutions of carbohydrates, or combinations of any two or more thereof.

18. A composition according to claim 1 wherein said agent is contained within said shell neat.

19. A composition according to claim 1 wherein said agent within said shell is dissolved or suspended in a biocompatible dispersing agent.

20. A composition according to claim 19 wherein said biocompatible dispersing agent is selected from soybean oil, mineral oil, corn oil, rapeseed oil, coconut oil, olive oil, safflower oil, cotton seed oil, aliphatic, cycloaliphatic or aromatic hydrocarbons having 4–30 carbon atoms, aliphatic or aromatic alcohols having 2–30 carbon atoms, aliphatic or aromatic esters having 2–30 carbon atoms, alkyl, aryl, or cyclic ethers having 2–30 carbon atoms, alkyl or aryl halides having 1–30 carbon atoms, optionally having more than one halogen substituent, ketones having 3–30 carbon atoms, polyalkylene glycol, or combinations of any two or more thereof.

21. A composition for in vivo delivery of imaging agent,
wherein said agent is a non-fluorinated solid, liquid, or gas and is substantially completely contained within a polymeric shell,
wherein the largest cross-sectional dimension of said shell is no greater than about 10 microns,
wherein said polymeric shell comprises a naturally occurring biocompatible polymer which is substantially crosslinked by way of disulfide bonds, and
wherein said polymeric shell containing agent therein is suspended in a biocompatible aqueous liquid wherein said disulfide bonds are crosslinked directly, that is, without a crosslinking agent being used.

22. A method to obtain in vivo magnetic resonance images by administering to a subject a composition as described in claim 1.

23. A method for the delivery of imaging agents to a subject, said method comprising administering to said subject an effective amount of composition according to claim 1.

* * * * *